(12) United States Patent
Chugh

(10) Patent No.: US 9,475,850 B2
(45) Date of Patent: Oct. 25, 2016

(54) METHODS FOR TREATMENT OF NEPHROTIC SYNDROME AND RELATED CONDITIONS

(75) Inventor: Sumant S. Chugh, Mountain Brook, AL (US)

(73) Assignee: THE UAB RESEARCH FOUNDATION, Birmingham, AL (US)

( * ) Notice: Subject to any disclaimer, the term of this patent is extended or adjusted under 35 U.S.C. 154(b) by 0 days.

(21) Appl. No.: 13/364,962

(22) Filed: Feb. 2, 2012

(65) Prior Publication Data
US 2013/0261054 A1 Oct. 3, 2013

Related U.S. Application Data

(63) Continuation of application No. PCT/US2011/039255, filed on Jun. 6, 2011.

(60) Provisional application No. 61/438,854, filed on Feb. 2, 2011, provisional application No. 61/351,866, filed on Jun. 5, 2010.

(51) Int. Cl.
| | |
|---|---|
| *A61K 38/38* | (2006.01) |
| *A61K 47/48* | (2006.01) |
| *C07K 14/76* | (2006.01) |
| *A61K 38/00* | (2006.01) |
| *A61P 7/08* | (2006.01) |
| *A61P 13/12* | (2006.01) |
| *A61P 3/06* | (2006.01) |
| *A61K 38/16* | (2006.01) |
| *C07K 1/00* | (2006.01) |
| *C07K 14/00* | (2006.01) |
| *C07K 16/00* | (2006.01) |
| *C07K 17/00* | (2006.01) |
| *A61K 35/00* | (2006.01) |
| *C07K 14/515* | (2006.01) |
| *C07K 14/435* | (2006.01) |
| *A61K 38/17* | (2006.01) |
| *C07K 14/575* | (2006.01) |
| *A61K 38/22* | (2006.01) |
| *C07K 14/72* | (2006.01) |

(52) U.S. Cl.
CPC ......... *C07K 14/435* (2013.01); *A61K 38/1709* (2013.01); *A61K 38/22* (2013.01); *C07K 14/515* (2013.01); *C07K 14/575* (2013.01); *C07K 14/72* (2013.01)

(58) Field of Classification Search
None
See application file for complete search history.

(56) References Cited

U.S. PATENT DOCUMENTS

| | | | |
|---|---|---|---|
| 2003/0228659 A1* | 12/2003 | Ballinger et al. | ............ 435/69.1 |
| 2007/0026002 A1 | 2/2007 | Gerber et al. | |
| 2011/0305663 A1* | 12/2011 | Gosselin et al. | ............ 424/85.2 |

FOREIGN PATENT DOCUMENTS

WO WO 2006014678 A2 * 2/2006 ............ C07K 14/47

OTHER PUBLICATIONS

Raju et al., "Glycoengineering of THerapeutic GLycoproteins: In Vitro Galactosylation and Sialylation of GLycoproteins with Terminal N-Acetylglucosamine and Galactose Residues," Biochemistry 40:8868-8876 (2001).*
Yin et al., "Genetic Variation in Angptl4 Provides Insights into Protein Processing and Function," J. Biol. Chem. 284:13213-13222 (2009).*
Zhu et al., "Angiopoietin-4: a decade of research," Biosci. Rep. 32:211-219 (2012).*
Yin et al., J. Biol. Chem. 284:13213-13222 (2009).*
Le Jan, et al. "Angiopoietin-Like 4 is a Proangiogenic Factor Produced during Ischemia and in Conventional Renal Cell Carcinoma" American Journal of Pathology, vol. 162, No. 5, May 2003; pp. 1521-1528.
Brenner, Barry M. "Brenner & Rector's The Kidney" Saunders Elsevier; 8th Edition; vol. 1; pp. 987-994.
Jackson, et al. "The codependence of angiogenesis and chronic inflammation" The FASEB Journal; vol. 11; May 1997; pp. 457-465.
Genbank Database, NCBI Acession No. NP_647475, version GI: 21536398 (first available 2002).
Yuan, et al. "Hypertriglyceridemia: its etiology, effects and treatment" Canadian Med. Assoc. J. 176:1113-1120 (2007).
Matthews, Brian W. "Structural and Genetic Analysis of Protein Stability" Annu. Rev. Biochem. 62:139-160 (1993).
Choi Sung Hee "Written Opinion of the International Searching Authority" Feb. 14, 2012; PCT/US2011/039255; pp. 1-4.
Clement, et al. "Podocyte-secreted angiopoietin-like-4 mediates proteinuria in glucocorticoid-sensitive nephrotic syndrome" Nature Medicine: vol. 17; No. 1; Jan. 2011; pp. 117-145.
Aich, et al. "Development of delivery methods for carbohydrate-based drugs: controlled release of biologically-active short chain fatty acid-hexosamine analogs" Glycoconj J.: May 11, 2010; pp. 1-11.

(Continued)

*Primary Examiner* — Hasan Ahmed
*Assistant Examiner* — Thea D'Ambrosio
(74) *Attorney, Agent, or Firm* — Thomas G. Peterson; Nicholas J. Landau; Bradley Arant Boult Cummings LLP

(57) ABSTRACT

The present disclosure provides a method for treating and/or preventing a condition characterized as a nephrotic syndrome, such as but not limited to minimal change disease (MCD) and membranous nephropathy (MN), and conditions related to nephrotic syndrome, such as but not limited to, proteinuria and edema, as well as diabetic nephropathy, diabetes mellitus, lupus nephritis or primary glomerular disease. The present disclosure further provides methods for reducing proteinuria and other disease states as discussed herein. Such methods comprise the therapeutic delivery of an Angptl4 polypeptide or Angptl4 polypeptide derivative to a subject.

20 Claims, 22 Drawing Sheets

(56) References Cited

OTHER PUBLICATIONS

Galeano, et al. "Mutation in the key enzyme of sialic acid biosynthesis causes severe glomerular proteinuria and is rescued by N-acetylmannosamine" The Journal of Clinical Investigation: vol. 17; No. 6; Jun. 2007; pp. 1585-1594.

Romeo, et al. "Population-based resequencing of ANGPTL4 uncovers variations that reduce triglycerides and increase HDL" Nature Genetics: vol. 39; No. 4; Apr. 2007; pp. 513-514.

Segen's Medical Dictionary, available online at http://medical-dictionary.thefreedictionary.com/p/administration, 3 pages at p. 1, lines 3-7, (2012).

Kita-Aoyama "Notice of Rejection—Japanese patent application No. 2013-513408" Japanese International Patent Bureau; Apr. 28, 2015; pp. 1-6.

Sun, H., et al. "Shenzangbing Yu Touxi Shenyizhi Zazhi" 2005, vol. 14, No. 6, pp. 531-535.

Sun, H., et al. "Enhanced Expression of ANGPTL2 in the Microvascular Lesions of Diabetic Glomerulopathy" Nephron Experimental Nephrology; 2007, vol. 105, pp. E117-E123.

Lee, E.C., et al. "Identification of a New Functional Domain in Angiopoietin-like 3 (ANGPTL3) and Angiopoietin-like 4 (ANGPTL4) Involved in Binding and Inhibition of Lipoprotein Lipase (LPL)" J. Biol. Chem., 2009, vol. 284, No. 20, pp. 13735-13745.

* cited by examiner

FIG. 3

| Gene / transgene | Species | Forward primer | Reverse primer | Taqman probe |
|---|---|---|---|---|
| Angptl4 | rat | tctgggatctccaccattttg | tcaccgtccagcctccat | caactgtgagatgacttc |
| Angptl4 | rat | cgccacccgcttacaca | cagaggctggatctggaaaagt | tgccaggaactcttt |
| aP2-Angptl4 construct | rat | tgttgatccagcccatgga | agggataggcttaccttcgaatg | cagcagcctccc |
| Prolactin (genomic) | rat | cttgaagggattgaaaagataattagc | ccatgagtcagaaaagcatgaac | aggtgagcattttcctg |

FIG. 5

SEQ ID NO: 1
MSGAPTAGAALMLCAATAVLLSAQGGPVQSKSPRFASWDEMNVLAHGLLQLGQGLREHAERTRSQLSALER
RLSACGSACQGTEGSTDLPLAPESRVDPEVLHSLQTQLKAQNSRIQQLFHKVAQQQRHLEKQHLRIQHLQSQFGLLD
HKHLDHEVAKPARRKRLPEMAQPVDPAHNVSRLHRLPRDCQELFQVGERQSGLFEIQPQGSPPFLVNCKMTSDGGWT
VIQRRHDGSVDFNRPWEAYKAGFGDPHGEFWLGLEKVHSITGDRNSRLAVQLRDWDGNAELLQFSVHLGGEDTAYSL
QLTAPVAGQLGATTVPPSGLSVPFSTWDQDHDLRRDKNCAKSLSGGWWFGTCSHSNLNGQYFRSIPQQRQKLKKGIF
WKTWRGRYYPLQATTMLIQPMAAEAAS
406 amino acids SEQ ID NO: 2
1       ataaaaaccg  tcctcgggcg  cggcggggag  aagccgagct  gagcggatcc  tcacacgact
61      gtgatccgat  tctttccagc  ggcttctgca  accaagcggg  tcttaccccc  ggtcctccgc
121     gtctccagtc  ctcgcacctg  gaacccaac   gtccccgaga  gtccccgaat  cccgctccc
181     aggctaccta  agaggatgag  cggtgctccg  acggccgggg  cagccctgat  gctctgcgcc
241     gccaccgccg  tgctactgag  cgctcagggc  ggacccgtgc  agtccaagtc  gccgcgcttt
301     gcgtcctggg  acgagatgaa  tgtcctggcg  cacggactcc  tgcagctcgg  ccaggggctg
361     cgcgaacacg  cggagcgcac  ccgcagtcag  ctgagcgcgc  tggagcggcg  cctgagcgcg
421     tgcgggtccg  cctgtcaggg  aaccgagggg  tccaccgacc  tcccgttagc  cctgagagc
481     cgggtggacc  ctgaggtcct  tcacagcctg  cagacacaac  tcaaggctca  gaacagcagg
541     atccagcaac  tcttccacaa  ggtggcccag  cagcagcggc  acctggagaa  gcagcacctg
601     cgaattcagc  atctgcaaag  ccagtttggc  ctcctggacc  acaagcacct  agaccatgag
661     gtggccaagc  ctgcccgaag  aaagaggctg  cccgagatgg  cccagccagt  tgaccggct
721     cacaatgtca  gccgcctgca  ccggctgccc  agggattgcc  aggagctgtt  ccaggttggg
781     gagaggcaga  gtggactatt  tgaaatccag  cctcagggt   ctccgccatt  tttggtgaac
841     tgcaagatga  cctcagatgg  aggctggaca  gtaattcaga  ggcgccacga  tggctcagtg
901     gacttcaacc  ggccctggga  agcctacaag  gcggggtttg  gggatcccca  cggcgagttc
961     tggctgggtc  tggagaaggt  gcatagcatc  acggggacc   gcaacagccg  cctggccgtg
1021    cagctgcggg  actgggatgg  caacgccgag  ttgctgcagt  tctccgtgca  cctgggtggc
1081    gaggacacgg  cctatagcct  gcagctcact  gcacccgtgg  ccggccagct  gggcgccacc
1141    accgtcccac  ccagcggcct  ctccgtaccc  ttctccactt  gggaccagga  tcacgacctc
1201    cgcagggaca  agaactgcgc  caagagcctc  tctggaggct  ggtggtttgg  cacctgcagc
1261    cattccaacc  tcaacggcca  gtacttccgc  tccatcccac  agcagcggca  gaagcttaag
1321    aagggaatct  tctggaagac  ctggcggggc  cgctactacc  cgctgcaggc  caccaccatg
1381    ttgatccagc  ccatggcagc  agaggcagcc  tctagcgtc   ctggctgggc  ctggtcccag
1441    gccacgaaa   gacggtgact  cttggctctg  ccgaggatg   tggccgttcc  ctgcctgggc
1501    aggggctcca  aggaggggcc  atctggaaac  ttgtggacag  agaagaagac  cacgactgga
1561    gaagcccct   ttctgagtgc  aggggggctg  catgcgttgc  ctcctgagat  cgaggctgca
1621    ggatatgctc  agactctaga  ggcgtggacc  aagggcatg   gagcttcact  ccttgctggc
1681    caggagttg   gggactcaga  gggaccactt  ggggccagcc  agactggcct  caatggcgga
1741    ctcagtcaca  ttgactgacg  ggaccagggc  cttgtgtggg  tcgagagcgc  cctcatggtg
1801    ctggtgctgt  tgtgtgtagg  tcccctgggg  acacaagcag  gcgccaatgg  tatctgggcg
1861    gagctcacag  agttcttgga  ataaagcaa   cctcagaaca  cttaaaaaaa  aaaaaaaaaa
1921    aaaaaaaaaa  aaaaaaaaaa  aaaaaaaaaa  aaaaaaaaaa  aaaaaaa SEQ ID NO: 3
MSGAPTAGAALMLCAATAVLLSAQGGPVQSKSPRFASWDEMNVLAHGLLQLGQGLREHAERTRSQLSALERRLSACG
SACQGTEGSTDLPLAPESRVDPEVLHSLQTQLKAQNSRIQQLFHKVAQQQRHLEKQHLRIQHLQSQFGLLDHKHLDH
EVAKPARRKRLPEMAQPVDPAHNVSRLHHGGWTVIQRRHDGSVDFNRPWEAYKAGFGDPHGEFWLGLEKVHSITGDR
NSRLAVQLRDWDGNAELLQFSVHLGGEDTAYSLQLTAPVAGQLGATTVPPSGLSVPFSTWDQDHDLRRDKNCAKSLS
GGWWFGTCSHSNLNGQYFRSIPQQRQKLKKGIFWKTWRGRYYPLQATTMLIQPMAAEAAS
368 amino acids

FIG 5 (CONT'D)

SEQ ID NO: 4

```
1     ataaaaaccg tcctcgggcg cggcggggag aagccgagct gagcggatcc tcacacgact
61    gtgatccgat tctttccagc ggcttctgca accaagcggg tcttacccc ggtcctccgc
121   gtctccagtc ctcgcacctg aaccccaac gtccccgaga gtccccgaat cccgctccc
181   aggctaccta agaggatgag cggtgctccg acggccgggg cagccctgat gctctgcgcc
241   gccaccgccg tgctactgag cgctcagggc ggacccgtgc agtccaagtc gccgcgcttt
301   gcgtcctggg acgagatgaa tgtcctggcg cacggactcc tgcagctcgg ccaggggctg
361   cgcgaacacg cggagcgcac ccgcagtcag ctgagcgcgc tggagcggcg cctgagcgcg
421   tgcgggtccg cctgtcaggg aaccgagggg tccaccgacc tcccgttagc ccctgagagc
481   cgggtggacc ctgaggtcct tcagcctg cagacacaac tcaaggctca gaacagcagg
541   atccagcaac tcttccacaa ggtggccag cagcagcggc acctggagaa gcagcacctg
601   cgaattcagc atctgcaaag ccagtttggc ctcctggacc acaagcacct agaccatgag
661   gtggccaagc ctgcccgaag aaagaggctg cccgagatgg cccagccagt tgacccggct
721   cacaatgtca gccgcctgca ccatggaggc tggacagtaa ttcagaggcg ccacgatggc
781   tcagtggact tcaaccggcc ctgggaagcc tacaaggcgg ggtttgggga tcccacggc
841   gagttctggc tgggtctgga aaggtgcat agcatcacgg gggaccgcaa cagccgcctg
901   gccgtgcagc tgcgggactg ggatggcaac gccgagttgc tgcagttctc cgtgcacctg
961   ggtggcgagg acacggccta tagcctgcag ctcactgcac ccgtggccgg ccagctgggc
1021  gccaccaccg tcccacccag cggcctctcc gtacccttct ccacttggga ccaggatcac
1081  gacctccgca gggacaagaa ctgcgccaag agcctctctg gaggctggtg gtttggcacc
1141  tgcagccatt ccaacctcaa cggccagtac ttccgctcca tcccacagca gcggcagaag
1201  cttaagaagg gaatcttctg gaagacctgg cggggccgct actacccgct gcaggccacc
1261  accatgttga tccagcccat ggcagcagag gcagcctcct agcgtcctgg ctggcctgg
1321  tcccaggccc acgaaagacg gtgactcttg gctctgcccg aggatgtggc cgttccctgc
1381  ctgggcaggg gctccaagga ggggccatct ggaaacttgt ggacagagaa gaagaccacg
1441  actggagaag ccccctttct gagtgcaggg gggctgcatg cgttgcctcc tgagatcgag
1501  gctgcaggat atgctcagac tctagaggcg tggaccaagg ggcatggagc ttcactcctt
1561  gctggccagg gagttgggga ctcagaggga ccacttgggg ccagcagac tggcctcaat
1621  ggcggactca gtcacattga ctgacgggga ccagggcttg tgtgggtcga gagcgccctc
1681  atggtgctgg tgctgttgtg tgtaggtccc ctggggacac aagcaggcgc caatggtatc
1741  tgggcggagc tcacagagtt cttggaataa aagcaacctc agaacactta aaaaaaaaaa
1801  aaaaaaaaaa aaaaaaaaaa aaaaaaaaaa aaaaaaaaaa aaaaaaaaaa aaa
```

SEQ ID NO: 5

MRCAPTAGAALVLCAATAGLLSAQGRPAQPEPPRFASWDEMNLLAHGLLQLGHGLREHVERTRGQLGALERRMAACG
NACQGPKGTDPKDRVPEGQAFETLQSLQTQLKAQNSKIQQLFQKVAQQQRYLSKQNLRIQNLQSQIDLLTPTHLDNG
VDKTSRGKRLPKMAQLIGLTPNATRLHRPPRDCQELFQEGERHSGLFQIQPLGSPPFLVNCEMTSDGGWTVIQRRLN
GSVDFNQSWEAYKDGFGDPQGEFWLGLEKMHSITGDRGSQLAVQLQDWDGNAKLLQFPIHLGGEDTAYSLQLTEPTA
NELGATNVSPNGLSLPFSTWDQDHDLRGDLNCAKSLSGGWWFGTCSHSNLNGQYFHSIPRQRQQRKKGIFWKTWKGR
YYPLQATTLLIQPMEATAAS
405 amino acids

FIG 5 (CONT'D)

SEQ ID NO: 6

```
1     atgcgctgcg ctccgaccgc aggcgctgct ctagtgctat gcgcagctactgcggggctg
61    ctgagcgcgc aagggcgccc tgcacagccg gagccgccgc gcttcgcatcctgggatgaa
121   atgaacttgc tggctcacgg gctgctgcag ctcggtcacg ggctgcgggaacacgtggag
181   cgcacccgtg gacagctggg cgcgctggaa cgccgcatgg ctgcctgcggtaacgcttgt
241   caggggccca aggggacaga cccgaaggat agagtccccg aaggccaggctcctgagact
301   ctgcagagtt tacagactca actcaaggct cagaacagca agatccagcaactgttccag
361   aaggtagccc agcagcagag atacctatca aagcagaatc tgagaatacagaatcttcag
421   agccagattg acctcttgac cccacacac ctagacaatg gggtagacaagacttcgagg
481   ggaaagaggc ttcccaagat ggcccagctc attggcttga ctcccaacgccacccgctta
541   cacaggcctc cccgggactg ccaggaactc tttcaagaag gggagcggcacagtggactt
601   ttccagatcc agcctctggg atctccacca tttttggtca actgtgagatgacttcagat
661   ggaggctgga cggtgattca gagacgcctg aacggctctg tggacttcaatcagtcttgg
721   gaagcctaca agatggcttt cggagatccc caaggcgagt tctggctggcctagagaag
781   atgcacagca tcacaggga ccgaggaagc cagttggctg tgcagctccaggactgggat
841   ggcaatgcca aattgctcca atttcctatc catttggggg gtgaggacacagcctacagc
901   ctgcagctca ccgagccac ggccaatgag ctgggtgcca ccaatgtttcccccaatggc
961   ctttccctgc ccttctctac ctgggaccaa gaccacgacc tccgagggaccttaactgt
1021  gccagagcc tctctggtgg ctggtggttt ggcacctgca gccattccaatctaaatgga
1081  caatacttcc actctattcc acggcaacgg cagcagcgta aaaaggggatcttctggaaa
1141  acatggaagg gccgctacta tccactacag gctaccaccc tgttgatccagcccatggag
1201  gctacagcag cctcttag
```

SEQ ID NO: 7

MRCAPTAGAALVLCAATAGLLSAQGRPAQPEPPRFASWDEMNLLAHGLLQLGHGLREHVERTRGQLGALERRMAACG
NACQGPKGKDAPFKDSEDRVPEGQTPETLQSLQTQLKAQNSKIQQLFQKVAQQQRYLSKQNLRIQNLQSIDLLAPT
HLDNGVDKTSRGKRLPKMTQLIGLTPNATHLHRPPRDCQELFQEGERHSGLFQIQPLGSPPFLVNCEMTSDGGWTVI
QRRLNGSVDFNQSWEAYKDGFGDPQGEFWLGLEKMHSITGNRGSQLAVQLQDWDGNAKLLQFPIHLGGEDTAYSLQL
TEPTANELGATNVSPNGLSLPFSTWDQDHDLRGDLNCAKSLSGGWWFGTCSHSNLNGQYFHSIPRQRQERKKGIFWK
TWKGRYYPLQATTLLIQPMEATAAS
410 amino acids

FIG. 5 (CONT'D)

SEQ ID NO: 8

```
   1    acgggctcca gatcttcttc tgcaccagag caagtctaag tctgagccggctcccccaga
  61    actccagctg ctgggtcttg aactcctgcg ttccggagtc ctagcgttgctgcacccaag
 121    gccaccccca gaatcatgcg ctgcgctccg acagcaggcg ctgccctggtgctatgcgcg
 181    gctactgcgg ggcttttgag cgcgcaaggg cgccctgcac agccagagccaccgcgcttt
 241    gcatcctggg acgagatgaa cttgctggct cacgggctgc tacagctcggccatgggctg
 301    cgcgaacacg tggagcgcac ccgtgggcag ctgggcgcgc tggagcgccgcatggctgcc
 361    tgtggtaacg cttgtcaggg gccaaggga aaagatgcac ccttcaaagactccgaggat
 421    agagtccctg aaggccagac tctgagact ctgcagagtt tgcagactcagctcaaggct
 481    caaaacagca agatccagca attgttccag aaggtggccc agcagcagatacctatca
 541    aagcagaatc tgagaataca gaatcttcag agccagatag acctcttggccccacgcac
 601    ctagacaatg gagtagacaa gacttcgagg ggaaagaggc ttcccagatgacccagctc
 661    attggcttga ctcccaacgc cacccactta cacaggccgc cccggactgccaggaactc
 721    ttccaagaag gggagaggca cagtggactt ttccagatcc agcctctggggtctccacca
 781    ttttggtca actgtgagat gacttcagat ggaggctgga cagtgattcagagacgcctg
 841    aacggctctg tggacttcaa ccagtcctgg gaagcctaca aggatggcttcggagatccc
 901    caaggcgagt tctggctggg cctggaaaag atgcacagca tcacagggaaccgaggaagc
 961    caattggctg tgcagctcca ggactgggat ggcaatgcca aattgctccaatttcccatc
1021    catttggggg gtgaggacac agcctacagc ctgcagctca ctgagccacgccaatgag
1081    ctgggtgcca ccaatgtttc ccccaatggc ctttccctgc ccttctctacttgggaccaa
1141    gaccatgacc tccgtgggga ccttaactgt gccaagagcc tctctggtggctggtggttt
1201    ggtacctgta gccattccaa tctcaatgga caatacttcc actctatcccacggcaacgg
1261    caggagcgta aaagggtat cttctggaaa acatggaagg gccgctactatcctctgcag
1321    gctaccaccc tgctgatcca gcccatggag gctacagcag cctcttagcctcctcactgg
1381    agcctggttc caggcctaag aagacagtga ctttggttgt ggccctgagatttggccatt
1441    ctctgctggg ggcaggagct ctaagtaggg ctatctgcgt cttgtggacaaagaagaagc
1501    ccgtaactgg agagactgga ggaccccttt tccgtgttgg ggtctgcaagcattgttgtc
1561    tgaaacagtc agagcaacag gaaacaaatg gcccagatcc agaaaacatggctcgaggg
1621    gcactgaata tcacttctcg cctaccagag aagttggga tgcagagggaccactacagt
1681    ccaactagct gggccctta tggcggactc agtcatattg actgactggagacagggtgc
1741    caggagccct ggatacactc atggtgctgt tgtaggtgct gtggatgcacaggtgctaac
1801    tgtggttccc aggcacaact cacagcattc ttacaataaa acaacctcagaacaaaaa
1861    aaaaaaaaa
```

SEQ ID NO: 9

MSGAPTAGAALMLCAATAVLLSAQGGPVQSKSPRFASWX$_{39}$X$_{40}$MNVLAHGLLQLGQGLREHAERTRSQLSALERRLSA
X$_{76}$GSAX$_{80}$QGTEGSTDLPLAPESRVDPEVLHSLQTQLKAQNSRIQQLFHKVAQQQRHLEKQHLRIQHLQSQFGLLDHK
HLDHEVAKPAX$_{161}$X$_{162}$X$_{163}$X$_{164}$LPEMAQPVDPAHNVSRLHRLPRDCQELFQVGERQSGLFEIQPQGSPPFLVNCKMTS
X$_{221}$GGWTVIQRRHDGSVDFNRPWEAYKAGFGDPHGEFWLGLEKVHSITGDRNSRLAVQLRDWDGNAELLQFSVHLGGE
DTAYSLQLTAPVAGQLGATTVPPSGLSVPFSTWDQDHDLRRDKNCAKSLSGGWWFGTCSHSNLNGQYFRSIPQQRQK
LKKGIFWKTWRGRYYPLQATTMLIQPMAAEEAAS
406 amino acids

SEQ ID NO: 10

MSGAPTAGAALMLCAATAVLLSAQGGPVQSKSPRFASWX$_{39}$X$_{40}$MNVLAHGLLQLGQGLREHAERTRSQLSALERRLSA
X$_{76}$GSAX$_{80}$QGTEGSTDLPLAPESRVDPEVLHSLQTQLKAQNSRIQQLFHKVAQQQRHLEKQHLRIQHLQSQFGLLDHK
HLDHEVAKPAX$_{161}$X$_{162}$X$_{163}$X$_{164}$LPEMAQPVDPAHNVSRLHHGGWTVIQRRHDGSVDFNRPWEAYKAGFGDPHGEFWLG
LEKVHSITGDRNSRLAVQLRDWDGNAELLQFSVHLGGEDTAYSLQLTAPVAGQLGATTVPPSGLSVPFSTWDQDHDL
RRDKNCAKSLSGGWWFGTCSHSNLNGQYFRSIPQQRQKLKKGIFWKTWRGRYYPLQATTMLIQPMAAEEAAS
368 amino acids

SEQUENCE LISTING

<160> NUMBER OF SEQ ID NOS: 83

<210> SEQ ID NO 1
<211> LENGTH: 406
<212> TYPE: PRT
<213> ORGANISM: Homo sapiens

<400> SEQUENCE: 1

```
Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu
        35                  40                  45

Leu Gln Leu Gly Gln Gly Leu Arg Glu His Ala Glu Arg Thr Arg Ser
    50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg Leu Pro Arg Asp Cys Gln Glu Leu Phe
            180                 185                 190

Gln Val Gly Glu Arg Gln Ser Gly Leu Phe Glu Ile Gln Pro Gln Gly
        195                 200                 205

Ser Pro Pro Phe Leu Val Asn Cys Lys Met Thr Ser Asp Gly Gly Trp
    210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro His Gly Glu Phe Trp
                245                 250                 255

Leu Gly Leu Glu Lys Val His Ser Ile Thr Gly Asp Arg Asn Ser Arg
            260                 265                 270

Leu Ala Val Gln Leu Arg Asp Trp Asp Gly Asn Ala Glu Leu Leu Gln
        275                 280                 285

Phe Ser Val His Leu Gly Gly Glu Asp Thr Ala Tyr Ser Leu Gln Leu
    290                 295                 300

Thr Ala Pro Val Ala Gly Gln Leu Gly Ala Thr Thr Val Pro Pro Ser
305                 310                 315                 320

Gly Leu Ser Val Pro Phe Ser Thr Trp Asp Gln Asp His Asp Leu Arg
                325                 330                 335

Arg Asp Lys Asn Cys Ala Lys Ser Leu Ser Gly Gly Trp Trp Phe Gly
            340                 345                 350

Thr Cys Ser His Ser Asn Leu Asn Gly Gln Tyr Phe Arg Ser Ile Pro
        355                 360                 365
```

| Gln | Gln | Arg | Gln | Lys | Leu | Lys | Lys | Gly | Ile | Phe | Trp | Lys | Thr | Trp | Arg |
| | 370 | | | | 375 | | | | | 380 | | | | | |

| Gly | Arg | Tyr | Tyr | Pro | Leu | Gln | Ala | Thr | Thr | Met | Leu | Ile | Gln | Pro | Met |
| 385 | | | | | 390 | | | | | 395 | | | | | 400 |

| Ala | Ala | Glu | Ala | Ala | Ser |
| | | | | | 405 |

<210> SEQ ID NO 2
<211> LENGTH: 1967
<212> TYPE: DNA
<213> ORGANISM: Homo sapiens

<400> SEQUENCE: 2

| ataaaaaccg tcctcgggcg cggcgggag aagccgagct gagcggatcc tcacacgact | 60 |
| gtgatccgat tctttccagc ggcttctgca accaagcggg tcttaccccc ggtcctccgc | 120 |
| gtctccagtc ctcgcacctg aaccccaac gtccccgaga gtccccgaat cccgctccc | 180 |
| aggctaccta agaggatgag cggtgctccg acggccgggg cagccctgat gctctgcgcc | 240 |
| gccaccgccg tgctactgag cgctcagggc ggacccgtgc agtccaagtc gccgcgcttt | 300 |
| gcgtcctggg acgagatgaa tgtcctggcg cacggactcc tgcagctcgg ccaggggctg | 360 |
| cgcgaacacg cggagcgcac ccgcagtcag ctgagcgcgc tggagcggcg cctgagcgcg | 420 |
| tgcgggtccg cctgtcaggg aaccgagggg tccaccgacc tcccgttagc ccctgagagc | 480 |
| cgggtggacc ctgaggtcct tcacagcctg cagacacaac tcaaggctca aacagcagg | 540 |
| atccagcaac tcttccacaa ggtggcccag cagcagcggc acctggagaa gcagcacctg | 600 |
| cgaattcagc atctgcaaag ccagtttggc ctcctggacc acaagcacct agaccatgag | 660 |
| gtggccaagc tgcccgaag aaagaggctg cccgagatgg cccagccagt tgacccggct | 720 |
| cacaatgtca gccgcctgca ccggctgccc agggattgcc aggagctgtt ccaggttggg | 780 |
| gagaggcaga gtggactatt tgaaatccag cctcaggggt ctccgccatt tttggtgaac | 840 |
| tgcaagatga cctcagatgg aggctggaca gtaattcaga ggcgccacga tggctcagtg | 900 |
| gacttcaacc ggccctggga agcctacaag gcggggttg gggatcccca cggcgagttc | 960 |
| tggctgggtc tggagaaggt gcatagcatc acggggacc gcaacagccg cctggccgtg | 1020 |
| cagctgcggg actgggatgg caacgccgag ttgctgcagt tctccgtgca cctgggtggc | 1080 |
| gaggacacgg cctatagcct gcagctcact gcacccgtgg ccggccagct gggcgccacc | 1140 |
| accgtcccac ccagcggcct ctccgtaccc ttctccactt gggaccagga tcacgacctc | 1200 |
| cgcagggaca agaactgcgc caagagcctc tctggaggct ggtggtttgg cacctgcagc | 1260 |
| cattccaacc tcaacggcca gtacttccgc tccatcccac agcagcggca gaagcttaag | 1320 |
| aagggaatct tctggaagac ctggcggggc cgctactacc cgctgcaggc caccaccatg | 1380 |
| ttgatccagc ccatggcagc agaggcagcc tcctagcgtc ctggctgggc ctggtcccag | 1440 |
| gcccacgaaa gacggtgact cttggctctg cccgaggatg tggccgttcc ctgcctgggc | 1500 |
| aggggctcca aggaggggcc atctggaaac ttgtggacag agaagaagac cacgactgga | 1560 |
| gaagcccct ttctgagtgc aggggggctg catgcgttgc ctcctgagat cgaggctgca | 1620 |
| ggatatgctc agactctaga ggcgtggacc aagggcatg gagcttcact ccttgctggc | 1680 |
| cagggagttg gggactcaga gggaccactt ggggccagcc agactggcct caatggcgga | 1740 |
| ctcagtcaca ttgactgacg gggaccaggg cttgtgtggg tcgagagcgc cctcatggtg | 1800 |
| ctggtgctgt tgtgtgtagg tcccctgggg acacaagcag gcgccaatgg tatctgggcg | 1860 |

```
gagctcacag agttcttgga ataaaagcaa cctcagaaca cttaaaaaaa aaaaaaaaa    1920 aaaaaaaaaa aaaaaaaaaa aaaaaaaaaa aaaaaaaaaa aaaaaaa                1967

<210> SEQ ID NO 3
<211> LENGTH: 368
<212> TYPE: PRT
<213> ORGANISM: Homo sapiens

<400> SEQUENCE: 3

Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
                20                  25                  30

Pro Arg Phe Ala Ser Trp Asp Glu Met Asn Val Leu Ala His Gly Leu
            35                  40                  45

Leu Gln Leu Gly Gln Gly Leu Arg Glu His Ala Glu Arg Thr Arg Ser
        50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg Gly Gly Trp Thr Val Ile Gln Arg Arg
            180                 185                 190

His Asp Gly Ser Val Asp Phe Asn Arg Pro Trp Glu Ala Tyr Lys Ala
        195                 200                 205

Gly Phe Gly Asp Pro His Gly Glu Phe Trp Leu Gly Leu Glu Lys Val
    210                 215                 220

His Ser Ile Thr Gly Asp Arg Asn Ser Arg Leu Ala Val Gln Leu Arg
225                 230                 235                 240

Asp Trp Asp Gly Asn Ala Glu Leu Leu Gln Phe Ser Val His Leu Gly
                245                 250                 255

Gly Glu Asp Thr Ala Tyr Ser Leu Gln Leu Thr Ala Pro Val Ala Gly
            260                 265                 270

Gln Leu Gly Ala Thr Thr Val Pro Pro Ser Gly Leu Ser Val Pro Phe
        275                 280                 285

Ser Thr Trp Asp Gln Asp His Asp Leu Arg Arg Asp Lys Asn Cys Ala
    290                 295                 300

Lys Ser Leu Ser Gly Gly Trp Trp Phe Gly Thr Cys Ser His Ser Asn
305                 310                 315                 320

Leu Asn Gly Gln Tyr Phe Arg Ser Ile Pro Gln Gln Arg Gln Lys Leu
                325                 330                 335
```

| Lys | Lys | Gly | Ile | Phe | Trp | Lys | Thr | Trp | Arg | Gly | Arg | Tyr | Tyr | Pro | Leu |
|---|---|---|---|---|---|---|---|---|---|---|---|---|---|---|---|
| | | | | 340 | | | | | 345 | | | | | 350 | |

| Gln | Ala | Thr | Thr | Met | Leu | Ile | Gln | Pro | Met | Ala | Ala | Glu | Ala | Ala | Ser |
|---|---|---|---|---|---|---|---|---|---|---|---|---|---|---|---|
| | | | 355 | | | | | 360 | | | | | 365 | | |

<210> SEQ ID NO 4
<211> LENGTH: 1853
<212> TYPE: DNA
<213> ORGANISM: Homo sapiens

<400> SEQUENCE: 4

```
ataaaaaccg tcctcgggcg cggcggggag aagccgagct gagcggatcc tcacacgact      60
gtgatccgat tctttccagc ggcttctgca accaagcggg tcttaccccc ggtcctccgc     120
gtctccagtc ctcgcacctg gaaccccaac gtccccgaga gtccccgaat ccccgctccc     180
aggctaccta agaggatgag cggtgctccg acggccgggg cagccctgat gctctgcgcc     240
gccaccgccg tgctactgag cgctcagggc ggacccgtgc agtccaagtc gccgcgcttt     300
gcgtcctggg acgagatgaa tgtcctggcg cacggactcc tgcagctcgg ccaggggctg     360
cgcgaacacg cggagcgcac ccgcagtcag ctgagcgcgc tggagcggcg cctgagcgcg     420
tgcgggtccg cctgtcaggg aaccgagggg tccaccgacc tccgttagcc cctgagagc      480 cgggtggacc ctgaggtcct tcacagcctg cagacacaac tcaaggctca gaacagcagg     540
atccagcaac tcttccacaa ggtggcccag cagcagcggc acctggagaa gcagcacctg     600
cgaattcagc atctgcaaag ccagtttggc ctcctggacc acaagcacct agaccatgag     660
gtggccaagc ctgcccgaag aaagaggctg cccgagatgg cccagccagt tgaccccggct     720 cacaatgtca gccgcctgca ccatggaggc tggacagtaa ttcagaggcg ccacgatggc     780
tcagtggact caaccggcc ctgggaagcc tacaaggcgg gtttgggga tccccacggc      840 gagttctggc tgggtctgga aaggtgcat agcatcacgg gggaccgcaa cagccgcctg     900
gccgtgcagc tgcgggactg ggatggcaac gccgagttgc tgcagttctc cgtgcacctg     960
ggtggcgagg acacggccta tagcctgcag ctcactgcac ccgtggccgg ccagctgggc    1020
gccaccaccg tcccacccag cggcctctcc gtacccttct ccacttggga ccaggatcac    1080
gacctccgca gggacaagaa ctgcgccaag agcctctctg gaggctggtg gtttggcacc    1140
tgcagccatt ccaacctcaa cggccagtac ttccgctcca tcccacagca gcggcagaag    1200
cttaagaagg gaatcttctg gaagacctgg cggggccgct actacccgct gcaggccacc    1260
accatgttga tccagcccat ggcagcagag gcagcctcct agcgtcctgg ctgggcctgg    1320
tcccaggccc acgaaagacg gtgactcttg gctctgcccg aggatgtggc cgttccctgc    1380
ctgggcaggg gctccaagga ggggccatct ggaaacttgt ggacagagaa gaagaccacg    1440
actggagaag ccccctttct gagtgcaggg gggctgcatg cgttgcctcc tgagatcgag    1500
gctgcaggat atgctcagac tctagaggcg tggaccaagg ggcatggagc ttcactcctt    1560
gctggccagg gagttgggga ctcagaggga ccacttgggg ccagccagac tggcctcaat    1620
ggcggactca gtcacattga ctgacgggga ccagggcttg tgtgggtcga gagcgccctc    1680
atggtgctgg tgctgttgtg tgtaggtccc ctggggacac aagcaggcgc caatggtatc    1740
tgggcggagc tcacagagtt cttggaataa aagcaacctc agaacactta aaaaaaaaa     1800 aaaaaaaaaa aaaaaaaaaa aaaaaaaaaa aaaaaaaaa aaaaaaaaa aaa            1853
```

```
<210> SEQ ID NO 5
<211> LENGTH: 405
<212> TYPE: PRT
<213> ORGANISM: Rattus norvegicus

<400> SEQUENCE: 5

Met Arg Cys Ala Pro Thr Ala Gly Ala Ala Leu Val Leu Cys Ala Ala
1               5                   10                  15

Thr Ala Gly Leu Leu Ser Ala Gln Gly Arg Pro Ala Gln Pro Glu Pro
            20                  25                  30

Pro Arg Phe Ala Ser Trp Asp Glu Met Asn Leu Leu Ala His Gly Leu
        35                  40                  45

Leu Gln Leu Gly His Gly Leu Arg Glu His Val Glu Arg Thr Arg Gly
    50                  55                  60

Gln Leu Gly Ala Leu Glu Arg Arg Met Ala Ala Cys Gly Asn Ala Cys
65                  70                  75                  80

Gln Gly Pro Lys Gly Thr Asp Pro Lys Asp Arg Val Pro Glu Gly Gln
                85                  90                  95

Ala Pro Glu Thr Leu Gln Ser Leu Gln Thr Gln Leu Lys Ala Gln Asn
            100                 105                 110

Ser Lys Ile Gln Gln Leu Phe Gln Lys Val Ala Gln Gln Gln Arg Tyr
        115                 120                 125

Leu Ser Lys Gln Asn Leu Arg Ile Gln Asn Leu Gln Ser Gln Ile Asp
    130                 135                 140

Leu Leu Thr Pro Thr His Leu Asp Asn Gly Val Asp Lys Thr Ser Arg
145                 150                 155                 160

Gly Lys Arg Leu Pro Lys Met Ala Gln Leu Ile Gly Leu Thr Pro Asn
                165                 170                 175

Ala Thr Arg Leu His Arg Pro Arg Asp Cys Gln Glu Leu Phe Gln
            180                 185                 190

Glu Gly Glu Arg His Ser Gly Leu Phe Gln Ile Gln Pro Leu Gly Ser
        195                 200                 205

Pro Pro Phe Leu Val Asn Cys Glu Met Thr Ser Asp Gly Gly Trp Thr
    210                 215                 220

Val Ile Gln Arg Arg Leu Asn Gly Ser Val Asp Phe Asn Gln Ser Trp
225                 230                 235                 240

Glu Ala Tyr Lys Asp Gly Phe Gly Asp Pro Gln Gly Glu Phe Trp Leu
                245                 250                 255

Gly Leu Glu Lys Met His Ser Ile Thr Gly Asp Arg Gly Ser Gln Leu
            260                 265                 270

Ala Val Gln Leu Gln Asp Trp Asp Gly Asn Ala Lys Leu Leu Gln Phe
        275                 280                 285

Pro Ile His Leu Gly Gly Glu Asp Thr Ala Tyr Ser Leu Gln Leu Thr
    290                 295                 300

Glu Pro Thr Ala Asn Glu Leu Gly Ala Thr Asn Val Ser Pro Asn Gly
305                 310                 315                 320

Leu Ser Leu Pro Phe Ser Thr Trp Asp Gln Asp His Asp Leu Arg Gly
                325                 330                 335

Asp Leu Asn Cys Ala Lys Ser Leu Ser Gly Gly Trp Trp Phe Gly Thr
            340                 345                 350

Cys Ser His Ser Asn Leu Asn Gly Gln Tyr Phe His Ser Ile Pro Arg
        355                 360                 365

Gln Arg Gln Gln Arg Lys Lys Gly Ile Phe Trp Lys Thr Trp Lys Gly
    370                 375                 380
```

Arg Tyr Tyr Pro Leu Gln Ala Thr Thr Leu Leu Ile Gln Pro Met Glu
385                 390                 395                 400

Ala Thr Ala Ala Ser
            405

<210> SEQ ID NO 6
<211> LENGTH: 1218
<212> TYPE: DNA
<213> ORGANISM: Rattus norvegicus

<400> SEQUENCE: 6

```
atgcgctgcg ctccgaccgc aggcgctgct ctagtgctat gcgcagctac tgcggggctg      60
ctgagcgcgc aagggcgccc tgcacagccg agccgccgc gcttcgcatc ctgggatgaa     120
atgaacttgc tggctcacgg gctgctgcag ctcggtcacg ggctgcggga acacgtggag     180
cgcacccgtg gacagctggg cgcgctggaa cgccgcatgg ctgcctgcgg taacgcttgt     240
caggggccca aggggacaga cccgaaggat agagtccccg aaggccaggc tcctgagact     300
ctgcagagtt tacagactca actcaaggct cagaacagca gatccagca actgttccag      360
aaggtagccc agcagcagag atacctatca aagcagaatc tgagaataca gaatcttcag     420
agccagattg acctcttgac ccccacacac ctagacaatg ggtagacaa gacttcgagg      480
ggaaagaggc ttcccaagat ggcccagctc attggcttga ctcccaacgc acccgctta     540
cacaggcctc cccgggactg ccaggaactc tttcaagaag gggagcggca cagtggactt     600
ttccagatcc agcctctggg atctccacca tttttggtca actgtgagat gacttcagat     660
ggaggctgga cggtgattca gagacgcctg aacggctctg tggacttcaa tcagtcttgg     720
gaagcctaca agatggcttt cggagatccc aaggcgagt tctggctggg cctagagaag     780
atgcacagca tcacagggga ccgaggaagc cagttggctg tgcagctcca ggactgggat     840
ggcaatgcca aattgctcca atttcctatc catttggggg gtgaggacac agcctacagc     900
ctgcagctca ccgagcccac ggccaatgag ctgggtgcca ccaatgtttc ccccaatggc     960
ctttccctgc ccttctctac ctgggaccaa gaccacgacc tccgagggga ccttaactgt    1020
gccaagagcc tctctggtgg ctggtggttt ggcacctgca gccattccaa tctaaatgga    1080
caatacttcc actctattcc acggcaacgg cagcagcgta aaaggggat cttctggaaa     1140
acatggaagg ccgctacta tccactacag ctaccaccc tgttgatcca gcccatggag     1200
gctacagcag cctcttag                                                   1218
```

<210> SEQ ID NO 7
<211> LENGTH: 410
<212> TYPE: PRT
<213> ORGANISM: Mus musculus

<400> SEQUENCE: 7

Met Arg Cys Ala Pro Thr Ala Gly Ala Ala Leu Val Leu Cys Ala Ala
1               5                   10                  15

Thr Ala Gly Leu Leu Ser Ala Gln Gly Arg Pro Ala Gln Pro Glu Pro
            20                  25                  30

Pro Arg Phe Ala Ser Trp Asp Glu Met Asn Leu Leu Ala His Gly Leu
        35                  40                  45

Leu Gln Leu Gly His Gly Leu Arg Glu His Val Glu Arg Thr Arg Gly
    50                  55                  60

Gln Leu Gly Ala Leu Glu Arg Arg Met Ala Ala Cys Gly Asn Ala Cys
65                  70                  75                  80

```
Gln Gly Pro Lys Gly Lys Asp Ala Pro Phe Lys Asp Ser Glu Asp Arg
                85                  90                  95
Val Pro Glu Gly Gln Thr Pro Glu Thr Leu Gln Ser Leu Gln Thr Gln
            100                 105                 110
Leu Lys Ala Gln Asn Ser Lys Ile Gln Gln Leu Phe Gln Lys Val Ala
        115                 120                 125
Gln Gln Gln Arg Tyr Leu Ser Lys Gln Asn Leu Arg Ile Gln Asn Leu
    130                 135                 140
Gln Ser Gln Ile Asp Leu Leu Ala Pro Thr His Leu Asp Asn Gly Val
145                 150                 155                 160
Asp Lys Thr Ser Arg Gly Lys Arg Leu Pro Lys Met Thr Gln Leu Ile
                165                 170                 175
Gly Leu Thr Pro Asn Ala Thr His Leu His Arg Pro Arg Asp Cys
            180                 185                 190
Gln Glu Leu Phe Gln Glu Gly Glu Arg His Ser Gly Leu Phe Gln Ile
        195                 200                 205
Gln Pro Leu Gly Ser Pro Pro Phe Leu Val Asn Cys Glu Met Thr Ser
    210                 215                 220
Asp Gly Gly Trp Thr Val Ile Gln Arg Arg Leu Asn Gly Ser Val Asp
225                 230                 235                 240
Phe Asn Gln Ser Trp Glu Ala Tyr Lys Asp Gly Phe Gly Asp Pro Gln
                245                 250                 255
Gly Glu Phe Trp Leu Gly Leu Glu Lys Met His Ser Ile Thr Gly Asn
            260                 265                 270
Arg Gly Ser Gln Leu Ala Val Gln Leu Gln Asp Trp Asp Gly Asn Ala
        275                 280                 285
Lys Leu Leu Gln Phe Pro Ile His Leu Gly Gly Glu Asp Thr Ala Tyr
    290                 295                 300
Ser Leu Gln Leu Thr Glu Pro Thr Ala Asn Glu Leu Gly Ala Thr Asn
305                 310                 315                 320
Val Ser Pro Asn Gly Leu Ser Leu Pro Phe Ser Thr Trp Asp Gln Asp
                325                 330                 335
His Asp Leu Arg Gly Asp Leu Asn Cys Ala Lys Ser Leu Ser Gly Gly
            340                 345                 350
Trp Trp Phe Gly Thr Cys Ser His Ser Asn Leu Asn Gly Gln Tyr Phe
        355                 360                 365
His Ser Ile Pro Arg Gln Arg Gln Glu Arg Lys Lys Gly Ile Phe Trp
    370                 375                 380
Lys Thr Trp Lys Gly Arg Tyr Tyr Pro Leu Gln Ala Thr Thr Leu Leu
385                 390                 395                 400
Ile Gln Pro Met Glu Ala Thr Ala Ala Ser
                405                 410

<210> SEQ ID NO 8
<211> LENGTH: 1869
<212> TYPE: DNA
<213> ORGANISM: Mus musculus

<400> SEQUENCE: 8
acgggctcca gatcttcttc tgcaccagag caagtctaag tctgagccgg ctcccccaga      60
actccagctg ctgggtcttg aactcctgcg ttccggagtc ctagcgttgc tgcacccaag     120
gccaccccca gaatcatgcg ctgcgctccg acagcaggcg ctgccctggt gctatgcgcg     180
gctactgcgg ggcttttgag cgcgcaaggg cgccctgcac agccagagcc accgcgcttt     240
```

```
gcatcctggg acgagatgaa cttgctggct cacgggctgc tacagctcgg ccatgggctg      300
cgcgaacacg tggagcgcac ccgtgggcag ctgggcgcgc tggagcgccg catggctgcc      360
tgtggtaacg cttgtcaggg gcccaaggga aaagatgcac ccttcaaaga ctccgaggat      420
agagtccctg aaggccagac tcctgagact ctgcagagtt tgcagactca gctcaaggct      480
caaaacagca agatccagca attgttccag aaggtggccc agcagcagag ataccctatca     540 aagcagaatc tgagaataca gaatcttcag agccagatag acctcttggc ccccacgcac      600
ctagacaatg gagtagacaa gacttcgagg ggaaagaggc ttcccaagat gacccagctc      660
attggcttga ctcccaacgc cacccactta cacaggccgc cccgggactg ccaggaactc      720
ttccaagaag gggagaggca cagtggactt ttccagatcc agcctctggg gtctccacca      780
tttttggtca actgtgagat gacttcagat ggaggctgga cagtgattca gagacgcctg      840
aacggctctg tggacttcaa ccagtcctgg gaagcctaca aggatggctt cggagatccc      900
caaggcgagt tctggctggg cctgaaaaag atgcacagca tcacagggaa ccgaggaagc      960
caattggctg tgcagctcca ggactgggat ggcaatgcca aattgctcca atttcccatc     1020
catttggggg gtgaggacac agcctacagc ctgcagctca ctgagcccac ggccaatgag     1080
ctgggtgcca ccaatgtttc ccccaatggc cttccctgc ccttctctac ttgggaccaa      1140
gaccatgacc tccgtgggga ccttaactgt gccaagagcc tctctggtgg ctggtggttt     1200
ggtacctgta gccattccaa tctcaatgga caatacttcc actctatccc acggcaacgg     1260
caggagcgta aaagggtat cttctggaaa acatggaagg gccgctacta tcctctgcag      1320
gctaccaccc tgctgatcca gcccatggag gctacagcag cctcttagcc tcctcactgg     1380
agcctggttc caggcctaag aagacagtga cttttggttgt ggccctgaga tttggccatt     1440
ctctgctggg ggcaggagct ctaagtaggg ctatctgcgt cttgtggaca agaagaagc      1500 ccgtaactgg agagactgga ggaccccttt tccgtgttgg ggtctgcaag cattgttgtc     1560
tgaaacagtc agagcaacag gaaacaaatg gcccagatcc agaaaacatg ggctcgaggg     1620
gcactgaata tcacttctcg cctaccagag aagttgggga tgcagaggga ccactacagt     1680
ccaactagct gggcccttaa tggcggactc agtcatattg actgactgga gacagggtgc     1740
caggagccct ggatacactc atggtgctgt tgtaggtgct gtggatgcac aggtgctaac     1800
tgtggttccc aggcacaact cacagcattc ttacaataaa aacaacctca gaacaaaaaa     1860
aaaaaaaaa                                                             1869

<210> SEQ ID NO 9
<211> LENGTH: 406
<212> TYPE: PRT
<213> ORGANISM: Homo sapiens
<220> FEATURE:
<221> NAME/KEY: MISC_FEATURE
<222> LOCATION: (39)..(39)
<223> OTHER INFORMATION: x = A, K, E or D
<220> FEATURE:
<221> NAME/KEY: MISC_FEATURE
<222> LOCATION: (40)..(40)
<223> OTHER INFORMATION: x = A, K, E or D
<220> FEATURE:
<221> NAME/KEY: MISC_FEATURE
<222> LOCATION: (76)..(76)
<223> OTHER INFORMATION: x = A or S
<220> FEATURE:
<221> NAME/KEY: MISC_FEATURE
<222> LOCATION: (80)..(80)
<223> OTHER INFORMATION: x = A or S
```

```
<220> FEATURE:
<221> NAME/KEY: MISC_FEATURE
<222> LOCATION: (161)..(161)
<223> OTHER INFORMATION: x = D, R, K, G, A, V or S
<220> FEATURE:
<221> NAME/KEY: MISC_FEATURE
<222> LOCATION: (162)..(162)
<223> OTHER INFORMATION: x = D, R, K, G, A, V or S
<220> FEATURE:
<221> NAME/KEY: MISC_FEATURE
<222> LOCATION: (163)..(163)
<223> OTHER INFORMATION: x = D, R, K, G, A, V or S
<220> FEATURE:
<221> NAME/KEY: MISC_FEATURE
<222> LOCATION: (164)..(164)
<223> OTHER INFORMATION: x = D, R, K, G, A, V or S
<220> FEATURE:
<221> NAME/KEY: misc_feature
<222> LOCATION: (221)..(221)
<223> OTHER INFORMATION: Xaa can be any naturally occurring amino acid

<400> SEQUENCE: 9

Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Xaa Xaa Met Asn Val Leu Ala His Gly Leu
        35                  40                  45

Leu Gln Leu Gly Gln Gly Leu Arg Glu His Ala Glu Arg Thr Arg Ser
    50                  55                  60

Gln Leu Ser Ala Leu Glu Arg Arg Leu Ser Ala Xaa Gly Ser Ala Xaa
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Xaa Xaa Xaa Xaa Leu Pro Glu Met Ala Gln Pro Val Asp Pro Ala His
                165                 170                 175

Asn Val Ser Arg Leu His Arg Leu Pro Arg Asp Cys Gln Glu Leu Phe
            180                 185                 190

Gln Val Gly Glu Arg Gln Ser Gly Leu Phe Glu Ile Gln Pro Gln Gly
        195                 200                 205

Ser Pro Pro Phe Leu Val Asn Cys Lys Met Thr Ser Xaa Gly Gly Trp
    210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro His Gly Glu Phe Trp
                245                 250                 255

Leu Gly Leu Glu Lys Val His Ser Ile Thr Gly Asp Arg Asn Ser Arg
            260                 265                 270

Leu Ala Val Gln Leu Arg Asp Trp Asp Gly Asn Ala Glu Leu Leu Gln
        275                 280                 285

Phe Ser Val His Leu Gly Gly Glu Asp Thr Ala Tyr Ser Leu Gln Leu
    290                 295                 300
```

```
Thr Ala Pro Val Ala Gly Gln Leu Gly Ala Thr Val Pro Pro Ser
305                 310                 315                 320

Gly Leu Ser Val Pro Phe Ser Thr Trp Asp Gln Asp His Asp Leu Arg
            325                 330                 335

Arg Asp Lys Asn Cys Ala Lys Ser Leu Ser Gly Gly Trp Trp Phe Gly
        340                 345                 350

Thr Cys Ser His Ser Asn Leu Asn Gly Gln Tyr Phe Arg Ser Ile Pro
    355                 360                 365

Gln Gln Arg Gln Lys Leu Lys Lys Gly Ile Phe Trp Lys Thr Trp Arg
370                 375                 380

Gly Arg Tyr Tyr Pro Leu Gln Ala Thr Thr Met Leu Ile Gln Pro Met
385                 390                 395                 400

Ala Ala Glu Ala Ala Ser
                405

<210> SEQ ID NO 10
<211> LENGTH: 368
<212> TYPE: PRT
<213> ORGANISM: Homo sapiens
<220> FEATURE:
<221> NAME/KEY: MISC_FEATURE
<222> LOCATION: (39)..(39)
<223> OTHER INFORMATION: x = A, K, D or E
<220> FEATURE:
<221> NAME/KEY: MISC_FEATURE
<222> LOCATION: (40)..(40)
<223> OTHER INFORMATION: x = A, K, D or E
<220> FEATURE:
<221> NAME/KEY: MISC_FEATURE
<222> LOCATION: (76)..(76)
<223> OTHER INFORMATION: x = A or C
<220> FEATURE:
<221> NAME/KEY: MISC_FEATURE
<222> LOCATION: (80)..(80)
<223> OTHER INFORMATION: x = A or C
<220> FEATURE:
<221> NAME/KEY: MISC_FEATURE
<222> LOCATION: (161)..(161)
<223> OTHER INFORMATION: x = D, R, K, G, A, V or S
<220> FEATURE:
<221> NAME/KEY: MISC_FEATURE
<222> LOCATION: (162)..(162)
<223> OTHER INFORMATION: x = D, R, K, G, A, V or S
<220> FEATURE:
<221> NAME/KEY: MISC_FEATURE
<222> LOCATION: (163)..(163)
<223> OTHER INFORMATION: x = D, R, K, G, A, V or S
<220> FEATURE:
<221> NAME/KEY: MISC_FEATURE
<222> LOCATION: (164)..(164)
<223> OTHER INFORMATION: x = D, R, K, G, A, V or S

<400> SEQUENCE: 10

Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
                20                  25                  30

Pro Arg Phe Ala Ser Trp Xaa Xaa Met Asn Val Leu Ala His Gly Leu
            35                  40                  45

Leu Gln Leu Gly Gln Gly Leu Arg Glu His Ala Glu Arg Thr Arg Ser
        50                  55                  60

Gln Leu Ser Ala Leu Glu Arg Arg Leu Ser Ala Xaa Gly Ser Ala Xaa
65                  70                  75                  80

Gln Gly Thr Glu Gly Ser Thr Asp Leu Pro Leu Ala Pro Glu Ser Arg
                85                  90                  95
```

-continued

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Xaa Xaa Xaa Xaa Leu Pro Glu Met Ala Gln Pro Val Asp Pro Ala His
                165                 170                 175

Asn Val Ser Arg Leu His His Gly Gly Trp Thr Val Ile Gln Arg Arg
            180                 185                 190

His Asp Gly Ser Val Asp Phe Asn Arg Pro Trp Glu Ala Tyr Lys Ala
        195                 200                 205

Gly Phe Gly Asp Pro His Gly Glu Phe Trp Leu Gly Leu Glu Lys Val
    210                 215                 220

His Ser Ile Thr Gly Asp Arg Asn Ser Arg Leu Ala Val Gln Leu Arg
225                 230                 235                 240

Asp Trp Asp Gly Asn Ala Glu Leu Leu Gln Phe Ser Val His Leu Gly
                245                 250                 255

Gly Glu Asp Thr Ala Tyr Ser Leu Gln Leu Thr Ala Pro Val Ala Gly
            260                 265                 270

Gln Leu Gly Ala Thr Thr Val Pro Pro Ser Gly Leu Ser Val Pro Phe
        275                 280                 285

Ser Thr Trp Asp Gln Asp His Asp Leu Arg Arg Asp Lys Asn Cys Ala
    290                 295                 300

Lys Ser Leu Ser Gly Gly Trp Trp Phe Gly Thr Cys Ser His Ser Asn
305                 310                 315                 320

Leu Asn Gly Gln Tyr Phe Arg Ser Ile Pro Gln Gln Arg Gln Lys Leu
                325                 330                 335

Lys Lys Gly Ile Phe Trp Lys Thr Trp Arg Gly Arg Tyr Tyr Pro Leu
            340                 345                 350

Gln Ala Thr Thr Met Leu Ile Gln Pro Met Ala Ala Glu Ala Ala Ser
        355                 360                 365

<210> SEQ ID NO 11
<211> LENGTH: 22
<212> TYPE: DNA
<213> ORGANISM: Homo sapiens

<400> SEQUENCE: 11
tctgggatct ccaccatttt tg                                          22

<210> SEQ ID NO 12
<211> LENGTH: 18
<212> TYPE: DNA
<213> ORGANISM: Homo sapiens

<400> SEQUENCE: 12
tcaccgtcca gcctccat                                               18

<210> SEQ ID NO 13
<211> LENGTH: 18
<212> TYPE: DNA
<213> ORGANISM: Homo sapiens

```
<400> SEQUENCE: 13
caactgtgag atgacttc                                                    18

<210> SEQ ID NO 14
<211> LENGTH: 17
<212> TYPE: DNA
<213> ORGANISM: Homo sapiens

<400> SEQUENCE: 14
cgccacccgc ttacaca                                                     17

<210> SEQ ID NO 15
<211> LENGTH: 22
<212> TYPE: DNA
<213> ORGANISM: Homo sapiens

<400> SEQUENCE: 15
cagaggctgg atctggaaaa gt                                               22

<210> SEQ ID NO 16
<211> LENGTH: 15
<212> TYPE: DNA
<213> ORGANISM: Homo sapiens

<400> SEQUENCE: 16
tgccaggaac tcttt                                                       15

<210> SEQ ID NO 17
<211> LENGTH: 23
<212> TYPE: DNA
<213> ORGANISM: Homo sapiens

<400> SEQUENCE: 17
tacaggctac caccctgttg atc                                              23

<210> SEQ ID NO 18
<211> LENGTH: 17
<212> TYPE: DNA
<213> ORGANISM: Homo sapiens

<400> SEQUENCE: 18
aaccgcgggc cctctag                                                     17

<210> SEQ ID NO 19
<211> LENGTH: 17
<212> TYPE: DNA
<213> ORGANISM: Homo sapiens

<400> SEQUENCE: 19
ccatggaggc tacagca                                                     17

<210> SEQ ID NO 20
<211> LENGTH: 27
<212> TYPE: DNA
<213> ORGANISM: Homo sapiens

<400> SEQUENCE: 20
cttgaaggga ttgaaaagat aattagc                                          27

<210> SEQ ID NO 21
<211> LENGTH: 24
<212> TYPE: DNA
<213> ORGANISM: Homo sapiens
```

<400> SEQUENCE: 21
ccatgagtca gaaaagcatt gaac                                          24

<210> SEQ ID NO 22
<211> LENGTH: 17
<212> TYPE: DNA
<213> ORGANISM: Homo sapiens

<400> SEQUENCE: 22
aggtgagcat tttcctg                                                  17

<210> SEQ ID NO 23
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 23

Gly Ala Ala Gly
1

<210> SEQ ID NO 24
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 24

Gly Ala Gly Ala
1

<210> SEQ ID NO 25
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 25

Gly Gly Ala Ala
1

<210> SEQ ID NO 26
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 26

Ala Gly Gly Ala
1

<210> SEQ ID NO 27
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 27

Ala Gly Ala Gly
1

```
<210> SEQ ID NO 28
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 28

Ala Ala Gly Gly
1

<210> SEQ ID NO 29
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 29

Gly Ala Ala Val
1

<210> SEQ ID NO 30
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 30

Gly Ala Val Ala
1

<210> SEQ ID NO 31
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 31

Gly Val Ala Ala
1

<210> SEQ ID NO 32
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 32

Ala Gly Val Ala
1

<210> SEQ ID NO 33
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 33

Ala Gly Ala Val
1
```

```
<210> SEQ ID NO 34
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 34

Ala Ala Val Gly
1

<210> SEQ ID NO 35
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 35

Ala Ala Gly Val
1

<210> SEQ ID NO 36
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 36

Ala Val Ala Gly
1

<210> SEQ ID NO 37
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 37

Ala Val Gly Ala
1

<210> SEQ ID NO 38
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 38

Val Gly Ala Ala
1

<210> SEQ ID NO 39
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 39

Val Ala Ala Gly
1
```

<210> SEQ ID NO 40
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 40

Val Ala Gly Ala
1

<210> SEQ ID NO 41
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 41

Gly Ala Val Val
1

<210> SEQ ID NO 42
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 42

Gly Val Ala Val
1

<210> SEQ ID NO 43
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 43

Gly Val Val Ala
1

<210> SEQ ID NO 44
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 44

Ala Gly Val Val
1

<210> SEQ ID NO 45
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 45

Ala Val Val Gly
1

-continued

<210> SEQ ID NO 46
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 46

Ala Val Gly Val
1

<210> SEQ ID NO 47
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 47

Val Gly Ala Val
1

<210> SEQ ID NO 48
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 48

Val Gly Val Ala
1

<210> SEQ ID NO 49
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 49

Val Ala Gly Val
1

<210> SEQ ID NO 50
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 50

Val Ala Val Gly
1

<210> SEQ ID NO 51
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 51

Val Val Gly Ala
1

<210> SEQ ID NO 52
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 52

Val Val Ala Gly
1

<210> SEQ ID NO 53
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 53

Gly Val Val Val
1

<210> SEQ ID NO 54
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 54

Val Gly Val Val
1

<210> SEQ ID NO 55
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 55

Val Val Val Gly
1

<210> SEQ ID NO 56
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 56

Val Val Gly Val
1

<210> SEQ ID NO 57
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 57

Gly Ala Ala Ala
1

```
<210> SEQ ID NO 58
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 58

Ala Gly Ala Ala
1

<210> SEQ ID NO 59
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 59

Ala Ala Ala Gly
1

<210> SEQ ID NO 60
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 60

Ala Ala Gly Ala
1

<210> SEQ ID NO 61
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 61

Ala Ala Val Val
1

<210> SEQ ID NO 62
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 62

Ala Ala Val Ala
1

<210> SEQ ID NO 63
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 63

Ala Ala Ala Val
1
```

-continued

```
<210> SEQ ID NO 64
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 64

Ala Val Ala Ala
1

<210> SEQ ID NO 65
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 65

Val Ala Ala Ala
1

<210> SEQ ID NO 66
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 66

Ala Val Val Val
1

<210> SEQ ID NO 67
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 67

Val Ala Val Val
1

<210> SEQ ID NO 68
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 68

Val Val Val Ala
1

<210> SEQ ID NO 69
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 69

Val Val Ala Val
1
```

```
<210> SEQ ID NO 70
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 70

Val Val Val Val
 1

<210> SEQ ID NO 71
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 71

Ser Ser Ser Ser
 1

<210> SEQ ID NO 72
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 72

Gly Gly Gly Gly
 1

<210> SEQ ID NO 73
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 73

Ala Ala Ala Ala
 1

<210> SEQ ID NO 74
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 74

Gly Ser Gly Ser
 1

<210> SEQ ID NO 75
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 75

Gly Ser Ser Gly
 1
```

```
<210> SEQ ID NO 76
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 76

Gly Gly Ser Ser
1

<210> SEQ ID NO 77
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 77

Ser Gly Ser Gly
1

<210> SEQ ID NO 78
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 78

Ser Gly Gly Ser
1

<210> SEQ ID NO 79
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 79

Ser Ser Gly Gly
1

<210> SEQ ID NO 80
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 80

Gly Ser Gly Gly
1

<210> SEQ ID NO 81
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 81

Ser Gly Gly Gly
1
```

```
<210> SEQ ID NO 82
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 82

Gly Gly Ser Gly
1

<210> SEQ ID NO 83
<211> LENGTH: 4
<212> TYPE: PRT
<213> ORGANISM: Artificial Sequence
<220> FEATURE:
<223> OTHER INFORMATION: Mutation at positions 161-164

<400> SEQUENCE: 83

Gly Gly Gly Ser
1
```

METHODS FOR TREATMENT OF NEPHROTIC SYNDROME AND RELATED CONDITIONS

CROSS-REFERENCE TO RELATED APPLICATIONS

This application is a continuation of International Application PCT/US11/39255, filed on Jun. 6, 2011 (currently pending). International Application PCT/US11/39255 cites for priority U.S. Application 61/351,866, filed Jun. 5, 2010. This application cites for priority U.S. Application 61/438,854, filed on Feb. 2, 2011. All of the above applications are incorporated herein in their entireties.

STATEMENT AS TO FEDERALLY SPONSORED RESEARCH

This invention was made with government support under grant numbers NIH 7R01DK077073-02 and NIH 1R56DK077073-01 awarded by the National Institutes of Health. The government has certain rights in the invention.

FIELD OF THE DISCLOSURE

The present disclosure is directed to methods for the treatment and prevention of nephrotic syndrome and conditions related thereto, such as, but not limited to, proteinuria and edema.

BACKGROUND

Nephrotic syndrome (NS) is a general term that refers to the loss of protein in the urine (proteinuria), hyperlipidemia (hypercholesterolemia and hypertriglyceridemia), and edema. Nephrotic syndrome involves changes in the pathology of cells in the kidney, such as podocytes. Proteinuria is defined as the presence of an excess of serum proteins in the urine. Albuminuria, a specific type of proteinuria, is a pathological condition wherein albumin is present in the urine.

Podocytes (or visceral epithelial cells) are cells in the outer layer of the glomerular capillary loop in the kidneys. The glomerulus filters blood, holding back large molecules such as proteins, and passing through small molecules such as water, salts, and sugar, as the first step in forming urine. The long processes, or "foot projections," of the podocytes wrap around the capillaries, and come to rest on the glomerular basement membrane. The foot processes are connected by a porous structure called the slit diaphragm. The innermost layer of the glomerular capillary loop is made of fenestrated endothelial cells. Kidneys affected by nephrotic syndrome have abnormalities in the glomerular capillary loop that cause leakage of blood proteins, resulting in proteinuria.

When protein is lost in the urine, its plasma concentration decreases, allowing water to move into other areas of the body, which leads to swelling known as edema. Edema is commonly observed in the feet and legs, in the belly or abdomen (ascites), and around the eyes, but can occur anywhere, especially in response to gravity. Additionally, because of this extra fluid that stays in the body, people often gain weight, experience fatigue and may find that they urinate less often Many conditions are categorized as nephrotic syndromes, including minimal change disease (MCD), focal segmental glomerulosclerosis (FSGS), membranous nephropathy (MN) (also called membranous glomerulonephritis, MGN), and membranoproliferative glomerulonephritis (MPGN). For years pathologists found no changes in MCD tissue when viewing specimens under light microscopy, hence the name minimal change disease. With the advent of electron microscopy, the changes now known as the hallmarks for the disease include diffuse loss of podocyte foot processes, vacuolation of the podocyte foot processes, and growth of microvilli on the visceral epithelial cells. Diabetic nephropathy is the most common cause of nephrotic syndrome.

Hypertriglyceridemia may occur due to changes in the activity of enzymes that degrade triglycerides, such as lipoprotein lipase (LPL) (2-4). Certain proteins involved in the etiology of nephrotic syndrome and proteinuria, such angiopoietin-like 4 (Angptl4), inhibit the activity of LPL.

The molecular basis of nephrotic syndrome is not known. Increased levels of Angptl4 have been noted in nephrotic syndrome, such as MCD, MN/MGN, and MPGN, but increased circulating levels of Angptl4 have not been associated with causation of proteinuria in nephrotic syndrome. However, the role of Angptl4 in nephrotic syndrome, such as but not limited to, MCD, FSGS, MN/MGN, and MPGN, and related conditions, such as, but not limited to, proteinuria have not been previously reported. Furthermore, the association of proteinuria and glucocorticoid sensitivity in nephrotic syndrome and the link between proteinuria and hypertriglyceridemia, two key components of nephrotic syndrome, have yet to be established. Therapy designed to reduce proteinuria further complicates the study of disease mechanisms. For example, glucocorticoids used to treat proteinuria in MCD independently raise plasma triglyceride levels (5), and normalization of plasma triglyceride levels lags behind the response of proteinuria to glucocorticoids in certain forms of nephrotic syndrome, such as MCD (6).

The present disclosure show that increased circulating levels of Angptl4 reduce the severity of nephrotic syndrome and conditions associated therewith, such as but not limited to, proteinuria. As a result, the present disclosure provides method for treating and/or preventing nephrotic syndrome, such as but not limited to, MCD, FSGS, MN/MGN, MPGN and diabetic nephropathy as well as methods of alleviating symptoms associated with nephrotic syndrome, including, but not limited to, proteinuria and edema. The present disclosure further provides methods for reducing proteinuria and edema.

BRIEF DESCRIPTION OF THE FIGURES

FIG. 1. shows the development and characterization of aP2-Angptl4 TG rats.

FIG. 2 shows the relationship of increased circulating levels of Angptl4 with proteinuria/albuminuria.

FIG. 4A shows reduction of proteinuria in Buffalo/Mna rats, a model of FSGS In the Buffalo/Mna rat model, assessment of baseline proteinuria was made on Day 0. Angptl4 or control protein were injected intra-peritoneally on two consecutive days (Days 1 & 2, arrows) into Buffalo Mna rats (n=4 rats/group). Proteinuria was assessed on alternate days, and expressed as a percentage of baseline values. Significant reduction in proteinuria was noted in recombinant Angptl4 treated rats.

FIG. 4B shows reduction of proteinuria in Thy1.1 nephritis, a short term model of mesangial injury. Thy1.1 nephritis was induced in male Wistar rats (n=4 rats/group). After assessment of baseline proteinuria (Day 1), concentrated supernatant protein from Angptl4 stable or control cell lines were injected intravenously on two consecutive days (Days 1 & 2, arrows) followed by assessment of proteinuria. Proteinuria was lower in Angptl4 treated rats throughout, and was statistically significant on Day 5. $*P<0.05$; $**P<0.01$. all values are mean±SE FIG. 5 shows the amino acid and cDNA sequences of Angptl4 from various species. SEQ ID NOS. 1 and 2 show amino acid and cDNA sequence from human (Protein Variant 1 isoform a, long form; underlined amino acid sequences at a position 40 and 161-164); SEQ ID NOS. 3 and 4 show amino acid and cDNA sequence from human (Protein Variant 3 isoform b, short form; underlined amino acid sequences at a position 40 and 161-164); SEQ ID NOS. 5 and 6 show amino acid and cDNA sequence from rat; SEQ ID NOS: 7 and 8 show amino acid and cDNA from mouse; underlined are forward sequencing primers. Bold are reverse sequencing primers.

SUMMARY OF THE DISCLOSURE

Figure 1A:
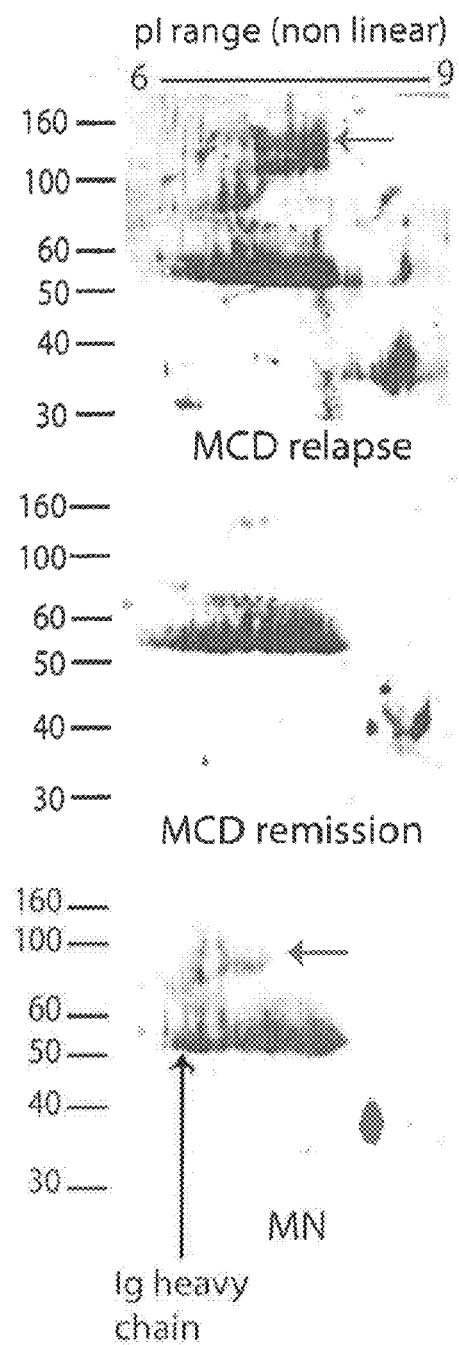
FIG. 1A shows a 2D gel analysis of 200 μg human plasma (n=4 patients/group, cropped representative blots shown) and demonstrates the presence of increased circulating levels of Angptl4 in patients with minimal change disease (MCD) in relapse and in patients with membranous nephropathy (MN) (indicated by arrows), compared to patients with MCD in remission (i.e. non proteinuric patients).

In a first aspect, the present disclosure provides methods of treatment and/or prevention of nephrotic syndrome. In one embodiment, the nephrotic syndrome is characterized as MCD, FSGS, MN/MGN, MPGN or diabetic nephropathy. In another embodiment, the nephrotic syndrome is characterized as MCD. In a further embodiment, the nephrotic syndrome is characterized as MSGS. In a further embodiment, the nephrotic syndrome is caused by a diabetic condition. In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4 or an Angptl4 polypeptide derivative. In still a further embodiment, the Angptl 4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration treats nephrotic syndrome by providing Angptl4 function. In an alternate embodiment, such administration treats nephrotic syndrome by providing a modified Angptl4 function, such as, but not limited to, an Angptl4 function that display reduced LPL inhibition or is resistant to cleavage.

In a second aspect, the present disclosure provides methods of treatment and/or prevention of MCD. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl 4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration treats MCD by providing Angptl4 function. In an alternate embodiment, such administration treats MCD by providing a modified Angptl4 function, such as, but not limited to, an Angptl4 function that display reduced LPL inhibition or is resistant to cleavage.

In a third aspect, the present disclosure provides methods of alleviating one or more symptoms of nephrotic syndrome, such as, but not limited to, proteinuria, hypercholesterolemia, hypertriglyceridemia and edema. In one embodiment, the nephrotic syndrome is characterized as MCD, FSGS, MN/MGN, MPGN and diabetic nephropathy. In another embodiment, the nephrotic syndrome is characterized as MCD. In a further embodiment, the nephrotic syndrome is caused by FSGS. In a further embodiment, the nephrotic syndrome is caused by a diabetic condition. In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl 4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration alleviates one or more symptoms of nephrotic syndrome by providing Angptl4 function. In an alternate embodiment, such administration alleviates one or more symptoms of nephrotic syndrome by providing a modified Angptl4 function, such as, but not limited to, an Angptl4 function that display reduced LPL inhibition or is resistant to cleavage.

In a fourth aspect, the present disclosure provides methods for reducing proteinuria in a subject. In one embodiment, the subject is suffering from nephrotic syndrome. In one embodiment, the nephrotic syndrome is characterized as MCD, FSGS, MN/MGN, MPGN and diabetic nephropathy. In another embodiment, the nephrotic syndrome is characterized as MCD. In another embodiment, the subject is suffering from a disorder characterized by proteinuria. In another embodiment, the subject is suffering from a diabetic condition. In a further embodiment, the proteinuria is caused by FSGS. In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl 4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration reduces proteinuria by providing Angptl4 function. In an alternate embodiment, such administration reduces proteinuria by providing a modified Angptl4 function, such as, but not limited to, an Angptl4 function that display reduced LPL inhibition or is resistant to cleavage.

In a fifth aspect, the present disclosure provides methods of reducing edema in a subject. In one embodiment, the subject is suffering from nephrotic syndrome. In one embodiment, the nephrotic syndrome is characterized as MCD, FSGS, MN/MGN, MPGN, and diabetic nephropathy. In another embodiment, the nephrotic syndrome is characterized as MCD. In a further embodiment, the nephrotic syndrome is caused by FSGS. In a specific embodiment, the edema is caused by decreased circulating levels of plasma proteins such as albumin. In a further embodiment, the nephrotic syndrome is caused by a diabetic condition In one embodiment, the diabetic condition is diabetic nephropathy, diabetes mellitus, lupus nephritis or primary glomerular disease. Reduction of proteinuria through the administration of an Angptl4 polypeptide of Angptl4 polypeptide derivative will reduce proteinuria, raise plasma protein levels and thereby reduce edema. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl 4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration reduces edema by providing Angptl4 function. In an alternate embodiment, such administration reduces edema by providing a modified Angptl4 function, such as, but not limited to, an Angptl4 function that display reduced LPL inhibition or is resistant to cleavage.

In a sixth aspect, the present disclosure provides methods of reducing hypercholesterolemia and/or hypertriglyceridemia in a subject. In one embodiment, the subject is suffering from nephrotic syndrome. In one embodiment, the nephrotic syndrome is characterized as MCD, FSGS, MN/MGN, MPGN and diabetic nephropathy. In another embodiment, the nephrotic syndrome is characterized as MCD. In a further embodiment, the nephrotic syndrome is caused by a diabetic condition In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl 4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration reduces hypercholesterolemia and/or hypertriglyceridemia by providing Angptl4 function. In an alternate embodiment, such administration reduces hypercholesterolemia and/or hypertriglyceridemia by providing a modified Angptl4 function, such as, but not limited to, an Angptl4 function that display reduced LPL inhibition or is resistant to cleavage.

In a seventh aspect, the present disclosure provides methods of treatment and/or prevention of a diabetic condition. In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl 4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration treats the foregoing conditions by providing Angptl4 function. In an alternate embodiment, such administration treats the foregoing conditions by providing a modified Angptl4 function, such as, but not limited to, an Angptl4 function that display reduced LPL inhibition or is resistant to cleavage.

In an eighth aspect, the present disclosure provides a pharmaceutical composition for use in the methods of the first through sixth aspects. The composition comprises one or more Anptl4 polypeptides or polypeptide derivatives. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl 4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein.

DETAILED DESCRIPTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

While investigating nephrotic syndrome, it was noted that Angptl4 secreted from podocytes induced proteinuria. More importantly, as described herein, circulating Angptl4 reduced the proteinuria in a transgenic animal model. Increased levels of Angptl 4 have been noted in nephrotic syndrome, such as MCD and MN, but increased circulating levels of Angptl4 have not been associated with causation of nephrotic syndrome.

While increased Angptl4 levels are shown to treat nephrotic syndrome and reduce associated proteinuria, increased Angptl4 in the circulation has been observed to induce hyperlipidemia (hypertriglyceridemia), such as, but not limited to, through inhibition of LPL. It would be advantageous to provide the benefits of increased circulating Angptl4 levels without the negative consequences of hyperlipidemia. Such an approach is possible using the Angptl4 polypeptide derivatives as disclosed herein.

Angiopoietin-like proteins have been implicated in the development of hypertriglyceridemia and tumor metastasis, and are functionally distinct from the angiopoietins. Angptl4 is a PPARγ (8) and PPARα (9) target gene highly expressed in the liver and adipose tissue, strongly induced by fasting in white adipose tissue and liver, and is an apoptosis survival factor for vascular endothelial cells under normoxic conditions (10). Angptl4 is a potent inhibitor of LPL (11), inducing significant hypertriglyceridemia following intravenous injection or adenovirus-mediated expression (12, 13). Other studies showed lesser expression of Angptl4 in cardiomyocytes and skeletal muscle, and low level expression in whole kidney on Northern blot analysis (8). Recent population based studies of the ANGPTL4 gene reveals variants that affect triglyceride levels in humans (14, 15).

The present disclosure shows a conclusive role for circulating Angptl4 in the reduction of proteinuria observed in nephrotic syndrome, such as, but not limited to, MCD, FSGS, MN, MPGN and diabetic nephropathy.

Definitions

The terms "prevention", "prevent", "preventing", "suppression", "suppress" and "suppressing" as used herein refer to a course of action (such as administering a compound or pharmaceutical composition) initiated prior to the onset of a symptom, aspect, or characteristics of a disease or condition so as to prevent or reduce such symptom, aspect, or characteristics. Such preventing and suppressing need not be absolute to be useful.

The terms "treatment", "treat" and "treating" as used herein refers a course of action (such as administering a compound or pharmaceutical composition) initiated after the onset of a symptom, aspect, or characteristics of a disease or condition so as to eliminate or reduce such symptom, aspect, or characteristics. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a disease or condition that is treatable by a method or compound of the disclosure.

The term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill, as the result of a disease or condition that is preventable by a method or compound of the disclosure.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

The term "therapeutically effective amount" as used herein refers to an amount of a compound, either alone or as a part of a pharmaceutical composition, that is capable of having any detectable, positive effect on any symptom, aspect, or characteristics of a disease or condition. Such effect need not be absolute to be beneficial. When referring to an Angptl4 polypeptide or Angptl4 polypeptide derivative, the term "therapeutically effective amount" refers to an amount of such polypeptide sufficient to reduce proteinuria in a subject.

The term "pharmaceutically acceptable derivative" means any pharmaceutically acceptable salt, ester, salt of an ester, solvate or other derivative of an Angptl4 polypeptide or polypeptide derivative of the present disclosure that, upon administration to a subject, is capable of providing (directly or indirectly) the function of wild type Angptl4; in certain embodiment, the Angptl4 polypeptide or polypeptide derivative shows decreased LPL inhibitory activity of a resistance to cleavage. Particularly favored derivatives are those that increase the bioavailability of an Angptl4 polypeptide or polypeptide derivative of the disclosure when such polypeptides are administered to a subject (e.g., by allowing an orally administered compound to be more readily absorbed into the blood), enhance delivery of such polypeptides to a given biological compartment, increase solubility to allow administration by injection, alter metabolism or alter rate of excretion. In one embodiment, the derivative is a prodrug.

The term "pharmaceutically acceptable salt(s)", unless otherwise indicated, includes salts of acidic or basic groups that may be present in the Angptl4 polypeptide or polypeptide derivative of the present disclosure.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. For biological systems, the term "about" refers to an acceptable standard deviation of error, preferably not more than 2-fold of a give value. Numerical quantities given herein are approximate unless stated otherwise, meaning that the term "about" or "approximately" can be inferred when not expressly stated.

Methods of Treatment and Prevention

The present disclosure provides methods of treatment and/or prevention of nephrotic syndrome. The present disclosure further provides methods of treatment and/or prevention of MCD, FSGS, and/or conditions with mesangial injury (such as diabetes mellitus). The present disclosure further provides methods of treatment and/or prevention of a diabetic condition. In one embodiment, the diabetic condition is diabetic nephropathy, diabetes mellitus, lupus nephritis or primary glomerular disease. The present disclosure additionally provides methods of alleviating one or more symptoms of nephritic syndrome, such as, but not limited to, proteinuria, hypercholesterolemia, hypertriglyceridemia and edema. Still further, the present disclosure provides for methods of reducing proteinuria. Further still, the present disclosure provides methods of reducing edema. The present disclosure additionally provides for pharmaceutical compositions comprising one or more Angptl4 polypeptides of Angptl4 polypeptide derivatives.

In one embodiment, the teachings of the present disclosure provide for the treatment and/or prevention of nephrotic syndrome in a subject in need of such treatment or prevention. In one embodiment, the nephrotic syndrome is characterized as MCD, FSGS, MN/MGN, and MPGN. In another embodiment, the nephrotic syndrome is characterized as MCD. In a further embodiment, the nephrotic syndrome is caused by FSGS. In a further embodiment, the nephrotic syndrome is caused by a diabetic condition. In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl 4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration treats nephrotic syndrome by providing Angptl4 function. In an alternate embodiment, such administration treats nephrotic syndrome by providing a modified Angptl4 function, such as, but not limited to, an Angptl4 function that display reduced LPL inhibition or is resistant to cleavage. Such method may further comprise identifying a subject in need of such treatment and/or prevention.

In an alternate embodiment, the teachings of the present disclosure provide for the treatment and/or prevention of MCD in a subject in need of such treatment or prevention. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl 4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration treats MCD by providing Angptl4 function. In an alternate embodiment, such administration treats MCD by providing a modified Angptl4 function, such as, but not limited to, an Angptl4 function that display reduced LPL inhibition or is resistant to cleavage. Such method may further comprise identifying a subject in need of such treatment and/or prevention.

In further embodiment, the teachings of the present disclosure provide for methods of alleviating one or more symptoms of nephrotic syndrome, such as, but not limited to, proteinuria, hypercholesterolemia, hypertriglyceridemia and edema. In one embodiment, the nephrotic syndrome is characterized as MCD, FSGS, MN/MGN, MPGN, and diabetic nephropathy. In another embodiment, the nephrotic syndrome is characterized as MCD. In a further embodiment, the nephrotic syndrome is caused by FSGS. In a further embodiment, the nephrotic syndrome is caused by a diabetic condition. In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl 4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration alleviates one or more symptoms of nephrotic syndrome by providing Angptl4 function. In an alternate embodiment, such administration alleviates one or more symptoms of nephrotic syndrome by providing a modified Angptl4 function, such as, but not limited to, an Angptl4 function that display reduced LPL inhibition or is resistant to cleavage. Such method may further comprise identifying a subject in need of such treatment and/or prevention.

In still a further embodiment, the teachings of the present disclosure provide methods for reducing proteinuria in a subject. In one embodiment, the subject is suffering from nephrotic syndrome. In one embodiment, the nephrotic syndrome is characterized as MCD, FSGS, MN/MGN, MPGN and diabetic nephropathy. In another embodiment, the nephrotic syndrome is characterized as MCD. In a further embodiment, the nephrotic syndrome is caused by FSGS. In a further embodiment, the nephrotic syndrome is caused by a diabetic condition. In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl 4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration reduces proteinuria by providing Angptl4 function. In an alternate embodiment, such administration reduces proteinuria by providing a modified Angptl4 function, such as, but not limited to, an Angptl4 function that display reduced LPL inhibition or is resistant to cleavage. Such method may further comprise identifying a subject in need of such treatment and/or prevention.

In yet a further embodiment, the teachings of the present disclosure provide methods for reducing edema in a subject. In one embodiment, the subject is suffering from nephrotic syndrome. In one embodiment, the nephrotic syndrome is characterized as MCD, FSGS, MN/MGN, MPGN and diabetic nephropathy. In another embodiment, the nephrotic syndrome is characterized as MCD. In a further embodiment, the nephrotic syndrome is caused by FSGS. In a further embodiment, the nephrotic syndrome is caused by a diabetic condition. In one embodiment, the diabetic condition is diabetic nephropathy, diabetes mellitus, lupus nephritis or primary glomerular disease. In a specific embodiment, the edema is caused by decreased circulating levels of plasma proteins such as albumin. Reduction of proteinuria through the administration of an Angptl4 polypeptide or a Angptl4 polypeptide derivative will raise reduce proteinuria, raise plasma protein levels and thereby reduce edema. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl 4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration reduces edema by providing Angptl4 function. In an alternate embodiment, such administration reduces edema by providing a modified Angptl4 function, such as, but not limited to, an Angptl4 function that display reduced LPL inhibition or is resistant to cleavage. Such method may further comprise identifying a subject in need of such treatment and/or prevention.

In still a further embodiment, the teachings of the present disclosure provide methods for reducing hypercholesterolemia and/or hypertriglyceridemia in a subject. In one embodiment, the subject is suffering from nephrotic syndrome. In one embodiment, the nephrotic syndrome is characterized as MCD, FSGS, MN/MGN, and MPGN. In another embodiment, the nephrotic syndrome is characterized as MCD. In a further embodiment, the nephrotic syndrome is caused by FSGS. In a further embodiment, the nephrotic syndrome is caused by a diabetic condition. In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl 4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration reduces proteinuria by providing Angptl4 function. In an alternate embodiment, such administration reduces proteinuria by providing a modified Angptl4 function, such as, but not limited to, an Angptl4 function that display reduced LPL inhibition or is resistant to cleavage. Such method may further comprise identifying a subject in need of such treatment and/or prevention.

In still a further embodiment, the teachings of the present disclosure provide methods for treatment and/or prevention of a nephrotic syndrome that is caused by a diabetic condition. In one embodiment, the diabetic condition is diabetic nephropathy, diabetes mellitus, lupus nephritis or primary glomerular disease. The methods comprise the step of administering to a subject an Angptl4 polypeptide or an Angptl4 polypeptide derivative. In one embodiment, the Angptl4 polypeptide comprises the sequence of SEQ ID NOS: 1, 3, 5, 7, 9 or 10. In an alternate, the amino acid sequence is a fragment of any of the foregoing sequences having an activity comparable to wild type Angptl4. In still a further embodiment, the Angptl 4 polypeptide derivative is a derivative described herein and has been modified to have decreased LPL inhibitory activity, to be resistant to cleavage, or a combination of the foregoing. The Angptl4 polypeptide or polypeptide derivative, in one embodiment, is sialylated. Such derivative may be based on any of the Angplt4 polypeptides described herein. The Angptl4 polypeptide or polypeptide derivative may be administered at a therapeutically effective dose, either alone, as a part of a pharmaceutical composition or in combination with a secondary agent. In one embodiment, such administration treats the foregoing conditions by providing Angptl4 function. In an alternate embodiment, such administration treats the foregoing conditions by providing a modified Angptl4 function, such as, but not limited to, an Angptl4 function that display reduced LPL inhibition or is resistant to cleavage.

Methods of Screening

The present disclosure also relates to a method for identifying a compound effective for treating or preventing nephrotic syndrome or a condition associated therewith, such as, but not limited to, proteinuria, hypercholesterolemia, hypertriglyceridemia or edema. In one embodiment, the nephrotic syndrome is characterized as MCD or MN. In another embodiment, the nephrotic syndrome is characterized as MCD. In another embodiment, the nephrotic syndrome is characterized by FSGS. In a further embodiment, the nephrotic syndrome is caused by a diabetic condition. In one embodiment, the diabetic condition is diabetic nephropathy, diabetes mellitus, lupus nephritis or primary glomerular disease. Such compounds may be useful as active ingredients included in pharmaceutical compositions or for administration alone. In one embodiment, the methods include determining the level a polypeptide involved in the etiology of nephrotic syndrome, such as, but not limited to, Angptl4.

In general, such screening methods comprises the steps of providing an assay system (as described in more detail below) that expresses a polypeptide involved in the etiology of nephrotic syndrome, such as, but not limited to, Angptl4, introducing into the assay system a test compound to be tested and determining whether the effect of the test compound on the level the polypeptide. The methods involve the identification of candidate or test compounds or agents (polypeptides, functional nucleic acids, carbohydrates, antibodies, small molecules or other molecules) which effect the level of sialylation of the polypeptide. Such compounds may then be further tested in appropriate systems (such as, but not limited to, the animal models systems described herein) to determine the activity of the identified compounds.

Candidate compounds are identified using a variety of assays, such as, but not limited to, assays that employ cells which express a polypeptide involved in the etiology of nephrotic syndrome, such as, but not limited to, Angptl4 or in assays with isolated polypeptides. The various assays can employ a variety of variants of such polypeptides (e.g., full-length, a biologically active fragment, or a fusion protein which includes all or a portion of the desired polypeptide). Moreover, such polypeptides can be derived from any suitable mammalian species (e.g., human, rat or murine); in a specific embodiment, the polypeptide is derived from a human.

Where the assay involves the use of a whole cell, the cell may either naturally express a polypeptide involved in the etiology of nephrotic syndrome, such as, but not limited to, Angptl4, or may be modified to express the same. In the latter case, cells can be modified to express a desired polypeptide through conventional molecular biology techniques, such as by infecting the cell with a virus comprising such polypeptide. The cell can also be a prokaryotic or an eukaryotic cell that has been transfected with a nucleotide sequence encoding such polypeptide. In the foregoing, full length polypeptides, fragments or fusion proteins containing at least a part of such polypeptide may be used. Exemplary assay systems are described in the current specification.

The various screening assays may be combined with an in vivo assay entailing measuring the effect of the test compound on the symptoms the disease states and conditions discussed herein. In such an embodiment, the compounds may be evaluated to determine if they impact a parameter associated with nephrotic syndrome or a condition related thereto, such as, but not limited to, proteinuria or edema. Such parameters include, but are not limited to, determining 1) the level of a polypeptide involved in the etiology of nephrotic syndrome and related conditions, such as, but not limited to Angptl4 and 2) determining the level of protein excretion, either total or with regard to specific components.

In one embodiment, such a screening assay can be performed, for example, by determining the level of a polypeptide, such as, but not limited to, Angptl4 and detecting a difference in the level of such polypeptide in the presence of as compared to the absence of a test compound. Such screening assay may be in vitro, in vivo or ex vivo and may be cell culture based (either with whole cells or lysates) or may be based on an animal model. Any assay of the present disclosure may be used in the foregoing method.

Suitable test compounds for use in the screening methods can be obtained from any suitable source, such as conventional compound libraries. The test compounds can also be obtained using any of the numerous approaches in combinatorial library methods known in the art, including: biological libraries, spatially addressable parallel solid phase or solution phase libraries, synthetic library methods requiring deconvolution, the "one-bead one-compound" library method and synthetic library methods using affinity chromatography selection. The biological library approach is limited to peptide libraries, while the other four approaches are applicable to peptide, non-peptide oligomer or small molecule libraries of compounds. Examples of methods for the synthesis of molecular libraries can be found in the art. Libraries of compounds may be presented in solution or on beads, bacteria, spores, plasmids or phage.

The present disclosure also provides kits for carrying out any method of the present disclosure, which can contain any of the compounds and/or compositions disclosed herein or otherwise useful for practicing a method of the disclosure.

Creation and Selection of Angptl4 Polypeptide Derivatives

Angiopoietin-related protein 4 is a polypeptide that in humans is encoded by the ANGPTL4 gene. This gene is a member of the angiopoietin/angiopoietin-like gene family and encodes a glycosylated, secreted protein with a N-terminal signal sequence (amino acid residues 1-22 of SEQ ID NO:1), a coiled-coil domain (amino acid residues 23-170 of SEQ ID NO:1), a linker region (amino acid residues 171-185 of SEQ ID NO:1) and a fibrinogen C-terminal domain (amino acid residues 186-406 of SEQ ID NO:1). This gene is induced under hypoxic conditions in endothelial cells and is the target of peroxisome proliferation activators. The encoded protein is a serum hormone directly involved in regulating glucose homeostasis, lipid metabolism, and insulin sensitivity and also acts as an apoptosis survival factor for vascular endothelial cells. Alternatively spliced transcript variants encoding different isoforms have been described. This gene was previously referred to as ANGPTL2 but has been renamed ANGPTL4.

Angptl4 inhibits LPL by breaking the LPL dimer molecule. Angptl4 has been unambiguously established as potent inhibitors of blood plasma triglyceride (TG) clearance, causing elevation of plasma TG levels. Recent evidence indicates that variations in the sequence of the Angptl4 polypeptide impact the effect on triglycerides, with certain mutations conferring reduced triglyceride levels implying a decreased inhibition of LPL (33 and 34, each of which are incorporated by reference for the teaching of Angptl4 variants). Furthermore, it has been reported that Angptl4 polypeptides exist in oligomeric forms and that oligomerization is required for inhibition of LPL activity. Once secreted from the cell, the oligomeric form is cleaved at a cleavage site ($R_{161}RKR_{164}$ of SEQ ID NOS: 1 and 3) to provide monomeric C-terminal forms and oligomeric N-terminal forms (34). The N-terminal residues 1-187 of the Angptl4 peptide were found to be sufficient to inhibit LPL (33).

The amino acid and cDNA sequences of the human, rat and mouse are provided in FIG. 5 and designated SEQ ID NOS: 1-8. The present disclosure contemplates the use of Angptl4 polypeptides and polypeptide derivatives in the methods disclosed herein, such as but not limited to, methods of treatment and prevention. As defined herein an Angptl4 polypeptide derivative refers to an Angptl4 polypeptide that includes one or more insertions, deletions and/or substitutions as determined from the amino acid sequence of the human polypeptides shown in SEQ ID NOS: 1 or 3 or the polypeptides shown in SEQ ID NOS: 5 or 7. In one embodiment, amino acid residues of the wild type Angptl 4 polypeptide are removed and replaced with different amino acid residues. The variants may be constructed as described herein or as known in the art. The variants so constructed may be evaluated using the methods and assays described herein to screen for activity.

When used herein, single letters when used to refer to amino acids have the following meanings:

| | | | |
|---|---|---|---|
| G | Glycine | P | Proline |
| A | Alanine | V | Valine |
| L | Leucine | I | Isoleucine |
| M | Methionine | C | Cysteine |
| F | Phenylalanine | Y | Tyrosine |
| W | Tryptophan | H | Histidine |
| K | Lysine | R | Arginine |
| Q | Glutamine | N | Asparagine |
| E | Glutamic Acid | D | Aspartic Acid |
| S | Serine | T | Threonine |

In one embodiment, the variant comprises a change in the amino acid sequence of an Angptl4 polypeptide that decreases the ability of Angptl4 to inhibit LPL or to or to be resistant to cleavage. The change may be a replacement, deletion and/or substitution of one or more residues in this region. Such changes have been described in the art (see references 33 and 34 which are herein incorporated by reference for such teaching). In one embodiment, such change occurs in residues 1-187 with respect to SEQ ID NO: 1 or residues 1-182 of SEQ ID NO: 3. In an alternate embodiment, such change occurs at position 40 with respect to SEQ ID NOS: 1, 3, 5 or 7 or SEQ ID NOS: 1 or 3. In one embodiment, the amino acid at position 40 (a negatively charged glutamic acid residue in wild-type Angptl4) is replaced with a neutral amino acid or a positively charged amino acid. In a particular embodiment, the change is an E40K substitution.

In another particular embodiment, the change is an E40A substitution. The E40K and E40A substitutions have been shown to reduce LPL inhibition by Angptl4, but not interfere with expression, secretion, processing and other functions of the polypeptide. In a further particular embodiment, the change at position 40 of SEQ ID NOS: 1 and 3 is selected from those shown in Table 1 below. In yet a further embodiment, the amino acid at position 39 (a negatively charged aspartic acid residue in wild-type Angptl4) is replaced with a neutral of positively charged amino acid. In one embodiment, the substitution is a D39K substitution of a D39A substitution. In a further particular embodiment, the change at position 39 of SEQ ID NOS: 1 and 3 is selected from those shown in Table 1 below. In certain embodiments, a polypeptide variant may contain one of the aforementioned changes at position 40, one of the aforementioned changes at position 39 or a combination of the foregoing. In a particular embodiment, the polypeptide contains a D39K substitution and a E40K substitution, a D39A substitution and a E40K substitution or a D39K substitution and an E40A substitution.

TABLE 1

Modifications of Positions 39-40 in the human Angptl4 protein

| G | P | V | L | I | M | C | F | Y |
|---|---|---|---|---|---|---|---|---|
| W | H | R | Q | N | S | T |   |   |

In another embodiment, the variant comprises one or more changes in a region of the Angptl4 polypeptide responsible for cleavage of the polypeptide. In one embodiment, this region is the $R_{161}RKR_{164}$ region of Angptl4 (corresponding to positions 161-164 of SEQ ID NO: 1). The change may be a replacement, deletion and/or substitution of one or more residues in this region. The $R_{161}RKR_{164}$ (positions 161-164 of SEQ ID NO: 1) region has been shown to be responsible for cleavage of the oligomeric forms of Angptl4, releasing oligomers of the N-terminal sequences and monomers of the C-terminal sequence. Forms of Angptl4 with a mutated cleavage site were shown to accumulate at higher levels in the circulation than wild-type polypeptide. Furthermore, preventing cleavage of the Angptl4 polypeptide stabilizes the oligomeric forms of Angptl4 observed to be efficacious in the present disclosure. In one embodiment, all 4 amino acid residues of the $R_{161}RKR_{164}$ (positions 161-164 of SEQ ID NO: 1) region are changed; in an alternate embodiment, 1, 2 or 3 amino acid residues of the $R_{161}RKR_{164}$ (positions 161-164 of SEQ ID NO: 1) region are changed. In a further embodiment, the arginine residues at positions 161, 162 or 164 are independently substituted with glycine, alanine, valine or serine and the lysine residue at position 163 is substituted with glycine, alanine, valine or serine. In a specific embodiment the $R_{161}RKR_{164}$ (positions 161-164 of SEQ ID NO: 1) amino acid sequence of SEQ ID NOS: 1 or 3 is replaced with $G_{161}AAG_{164}$ (SEQ ID NO: 29); in a further specific embodiment, the $R_{161}RKR_{164}$ amino acid sequence of SEQ ID NOS: 1 or 3 is replaced with $G_{161}SGS_{164}$ (SEQ ID NO: 80). Exemplary amino acid sequences for replacement of the entire $R_{161}RKR_{164}$ (positions 161-164 of SEQ ID NO: 1) region of SEQ ID NOS: 1 or 3 is provided in Table 2 below.

TABLE 2

Modifications of $_{161}RRKR_{164}$ in the human Angptl4 protein

| SEQ ID |      |
|--------|------|
| 29     | GAAG |
| 30     | GAGA |
| 31     | GGAA |
| 32     | AGGA |
| 33     | AGAG |
| 34     | AAGG |
| 35     | VGAA |
| 36     | VAAG |
| 37     | VAGA |
| 38     | GAAV |
| 39     | GAVA |
| 40     | GVAA |
| 41     | AGVA |
| 42     | AGAV |
| 43     | AAVG |
| 44     | AAGV |
| 45     | AVAG |
| 46     | AVGA |
| 47     | GAVV |
| 48     | GVAV |
| 49     | GVVA |
| 50     | AGVV |
| 51     | AVVG |
| 52     | AVGV |
| 53     | VGAV |
| 54     | VGVA |
| 55     | VAGV |
| 56     | GVVV |
| 57     | VGVV |
| 58     | VVVG |
| 59     | VVGV |
| 60     | VAVG |
| 61     | VVGA |
| 62     | VVAG |
| 63     | VVVA |
| 64     | VVAV |
| 65     | GAAA |
| 66     | AGAA |
| 67     | AAAG |
| 68     | AAGA |
| 69     | AAVV |
| 70     | AAVA |
| 71     | AAAV |
| 72     | AVAA |
| 73     | VAAA |
| 74     | AVVV |
| 75     | VAVV |

TABLE 2-continued

| Modifications of $_{161}RRKR_{164}$ in the human Angptl4 protein | |
|---|---|
| SEQ ID | |
| 76 | VVVV |
| 77 | SSSS |
| 78 | GGGG |
| 79 | AAAA |
| 80 | GSGS |
| 81 | GSSG |
| 82 | GGSS |
| 83 | SGSG |
| 84 | SGGS |
| 85 | SSGG |
| 86 | GSGG |
| 87 | SGGG |
| 88 | GGSG |
| 89 | GGGS |
| 90 | VAVA |

In a further embodiment, one or more of the amino acids in the $R_{161}RKR_{164}$ amino acid sequence of SEQ ID NOS: 1 or 3 altered to remove a consensus binding site of an enzyme capable of cleaving Angplt4, such that Angptl4 is resistant to cleavage. In one embodiment, the enzyme is a proprotein convertase and the consensus binding site is RXKR, RXRR, RR or KR, where X is any amino acid. In making such alternations, one or more amino acids may be deleted or substituted with glycine, alanine, valine or serine or with any of the other substitutions discussed herein.

In still a further embodiment, the variant comprises one or more changes in a region of the Angptl4 polypeptide responsible for oligomerization of the polypeptide. In one embodiment, this region is the $C_{76}$ and/or $C_{80}$ region of Angptl4. The $C_{76}$ and/or $C_{80}$ region has been shown to be involved in oligomerization of the Angptl4 polypeptide (34, which reference is incorproated herein for such teaching). The change may be a replacement, deletion and/or substitution of one or more residues in this region. In a particular embodiment, only one of the cysteine residues at positions 76 and 80 is substituted; in an alternate embodiment, both cysteine residues at positions 76 and 80 are both substituted. In one embodiment, at least one of the cysteine residues at position 76 and 80 are substituted independently with alanine or serine; in another embodiment, both cysteine residues are substituted with alanine or serine.

In a further embodiment, the variant comprises one or more changes in the $R_{161}RKR_{164}$ region of Angplt4 that inhibits the cleavage of the Angptl4 polypeptide oligomer and a change at position 40 that reduces inhibition of LPL activity by Angptl4. Any of the changes discussed herein are included.

In one embodiment, the present disclosure provides for Angptl4 polypeptide variants having the amino acid sequence of SEQ ID NOS: 9 or 10. SEQ ID NO: 9 is shown in FIG. 5 and includes the wild type sequence of Angptl4 from SEQ ID NO: 1, with the exception of substitutions at positions 39, 40, 76, 80 and 161-164 indicated by $X_{39}$, $X_{40}$, $X_{76}$, $X_{80}$, $X_{161}$, $X_{162}$, $X_{163}$ and $X_{164}$, respectively. SEQ ID NO: 10 is shown in FIG. 5 and includes the wild type sequence of Angptl4 from SEQ ID NO: 3, with the exception of substitutions at positions 39, 40, 76, 80 and 161-164 indicated by $X_{39}$, $X_{40}$, $X_{76}$, $X_{80}$, $X_{161}$, $X_{162}$, $X_{163}$ and $X_{164}$, respectively.

In SEQ ID NOS: 9 and 10, $X_{39}$ may be A, G, P, V, L, I, M, C, F, Y, W, H, R, Q, N, S, T or K. In one embodiment, $X_{39}$ is a neutral or positively charged amino acid. In a further embodiment, $X_{39}$ may be A or K. In still a further embodiment, $X_{39}$ may be D.

In SEQ ID NOS: 9 and 10, $X_{40}$ may be A, G, P, V, L, I, M, C, F, Y, W, H, R, Q, N, S, T or K. In one embodiment, $X_{40}$ is a neutral or positively charged amino acid. In a further embodiment, $X_{40}$ may be A or K. In still a further embodiment, $X_{40}$ may be E. In yet a further embodiment, $X_{40}$ may be E when $X_{39}$ is not D and $X_{39}$ may be D when $X_{40}$ is not E.

In SEQ ID NOS: 9 and 10, at least one of $X_{76}$ and $X_{80}$ may be substituted. In one embodiment, $X_{76}$ and $X_{80}$ are independently A or S or C. In one embodiment, one of $X_{76}$ and $X_{80}$ may be A or S and the other of $X_{76}$ and $X_{80}$ is C. In a further embodiment, both of $X_{76}$ and $X_{80}$ may be independently A or S. In still a further embodiment, both of $X_{76}$ and $X_{80}$ may C.

In SEQ ID NOS: 9 and 10, at least one of $X_{161}$, $X_{162}$, $X_{163}$ and $X_{164}$ may be substituted. In one embodiment, all 4 of $X_{161}$, $X_{162}$, $X_{163}$ and $X_{164}$ are substituted; in an alternate embodiment, 1, 2 or 3 of $X_{161}$, $X_{162}$, $X_{163}$ and $X_{164}$ are substituted. In a further embodiment, $X_{161}$, $X_{162}$, $X_{163}$ and $X_{164}$ are independently D, R, K, G, A, V or S. In still a further embodiment, all 4 of are substituted with the combinations recited in Table 2.

The present disclosure contemplates combinations of the foregoing in any form. Furthermore, the designated residues in SEQ ID NOS: 9 and 10 may be substituted with conservative amino acid substitutions as designated in Table 3, or with residues having a difference in hydropathic index of +/−1 or less or with residues having a difference in hydrophilicity values of +/−1 or less.

In a one embodiment, $X_{39}$ is D, $X_{40}$ is A or K, $X_{76}$ and $X_{80}$ are C and $X_{161}$, $X_{162}$, $X_{163}$ and $X_{164}$ are independently substituted with D, R, K, G, A, V or S, optionally provided that at least one of $X_{161}$, $X_{162}$, $X_{163}$ and $X_{164}$ is an amino acid not found in SEQ ID NOS: 1 or 3. In another embodiment, $X_{39}$ is D, $X_{40}$ is A or K, $X_{76}$ and $X_{80}$ are C and $X_{161}$, $X_{162}$, $X_{163}$ and $X_{164}$ are selected from the combinations shown in Table 2. In still another embodiment, $X_{39}$ is D, $X_{40}$ is A or K, $X_{76}$ and $X_{80}$ are C and $X_{161}$, $X_{162}$, $X_{163}$ and $X_{164}$ are GSGS or GAAG.

In an additional embodiment, $X_{39}$ is D, $X_{40}$ is A or K, one of $X_{76}$ and $X_{80}$ is A or S and the other of $X_{76}$ and $X_{80}$ is C and $X_{161}$, $X_{162}$, $X_{163}$ and $X_{164}$ are independently substituted with D, R, K, G, A, V or S, optionally provided that at least one of $X_{161}$, $X_{162}$, $X_{163}$ and $X_{164}$ is an amino acid not found in SEQ ID NOS: 1 or 3. In a further embodiment, $X_{39}$ is D, $X_{40}$ is A or K, one of $X_{76}$ and $X_{80}$ is A or S and the other of $X_{76}$ and $X_{80}$ is C and $X_{161}$, $X_{162}$, $X_{163}$ and $X_{164}$ are selected from the combinations shown in Table 2. In still a further embodiment, $X_{39}$ is D, $X_{40}$ is A or K, one of $X_{76}$ and $X_{80}$ is A or S and the other of $X_{76}$ and $X_{80}$ is C and $X_{161}$, $X_{162}$, $X_{163}$ and $X_{164}$ are GSGS or GAAG.

In one embodiment, $X_{39}$ is A or K, $X_{40}$ is E, $X_{76}$ and $X_{80}$ are C and $X_{161}$, $X_{162}$, $X_{163}$ and $X_{164}$ are independently substituted with D, R, K, G, A, V or S, optionally provided that at least one of $X_{161}$, $X_{162}$, $X_{163}$ and $X_{164}$ is an amino acid not found in SEQ ID NOS: 1 or 3. In another embodiment, $X_{39}$ is A or K, $X_{40}$ is E, $X_{76}$ and $X_{80}$ are C and $X_{161}$, $X_{162}$, $X_{163}$ and $X_{164}$ are selected from the combinations shown in Table 2. In still another embodiment, $X_{39}$ is A or K, $X_{40}$ is E, $X_{76}$ and $X_{80}$ are C and $X_{161}$, $X_{162}$, $X_{163}$ and $X_{164}$ are GSGS or GAAG.

In one embodiment, $X_{39}$ is D, $X_{40}$ is K, $X_{76}$ and $X_{80}$ are C and $X_{161}$, $X_{162}$, $X_{163}$ and $X_{164}$ are independently substituted with D, R, K, G, A, V or S, optionally provided that at least one of $X_{161}$, $X_{162}$, $X_{163}$ and $X_{164}$ is an amino acid not found in SEQ ID NOS: 1 or 3. In another embodiment, $X_{39}$ is D, $X_{40}$ is K, $X_{76}$ and $X_{80}$ are C and $X_{161}$, $X_{162}$, $X_{163}$ and $X_{164}$ are selected from the combinations shown in Table 2. In still another embodiment, $X_{39}$ is D, $X_{40}$ is K, $X_{76}$ and $X_{80}$ are C and $X_{161}$, $X_{162}$, $X_{163}$ and $X_{164}$ are GSGS or GAAG.

In one embodiment, $X_{39}$ is D, $X_{40}$ is K, one of $X_{76}$ and $X_{80}$ is A or S and the other of $X_{76}$ and $X_{80}$ is C and $X_{161}$, $X_{162}$, $X_{163}$ and $X_{164}$ are independently substituted with D, R, K, G, A, V or S, optionally provided that at least one of $X_{161}$, $X_{162}$, $X_{163}$ and $X_{164}$ is an amino acid not found in SEQ ID NOS: 1 or 3. In another embodiment, $X_{39}$ is D, $X_{40}$ is K, one of $X_{76}$ and $X_{80}$ is A or S and the other of $X_{76}$ and $X_{80}$ is C and $X_{161}$, $X_{162}$, $X_{163}$ and $X_{164}$ are selected from the combinations shown in Table 2. In still another embodiment, $X_{39}$ is D, $X_{40}$ is K, one of $X_{76}$ and $X_{80}$ is A or S and the other of $X_{76}$ and $X_{80}$ is C and $X_{161}$, $X_{162}$, $X_{163}$ and $X_{164}$ are GSGS or GAAG.

In one embodiment, the Angptl4 derivative is based on a fragment of Angplt4. Suitable fragments include any fragment that retains the activity of wild type Angplt4 or any fragment of 100 or more consecutive amino acids. In one embodiment, such fragment is based on amino acids 1-187 SEQ ID NO: 1 or amino acids 1-182 of SEQ ID NO: 3. Such fragments may have the amino acid substitutions described in the preceding paragraphs.

The Angptl4 polypeptide derivative may have an activity that is comparable to or increased (in one embodiment, 50% or more) as compared to the wild-type Angptl4 polypeptide activity; alternatively, the Angptl4 polypeptide derivative may have an activity that is decreased (in one embodiment, less than 50%) as compared to the wild-type Angptl4 polypeptide activity. In a specific embodiment, the Angptl4 polypeptide derivative has a decreased ability to inhibit LPL and shows an increased resistance to cleavage.

The deletions, additions and substitutions can be selected, as would be known to one of ordinary skill in the art, to generate a desired Angptl4 polypeptide derivative. For example, conservative substitutions or substitutions of amino acids with similar properties are expected to be tolerated. In addition, specific deletions, insertions and substitutions may impact, positively or negatively, a certain Angptl4 polypeptide activity but not impact a different Angptl4 polypeptide activity.

Conservative modifications to the amino acid sequence of any of SEQ ID NOS: 1 or 3 or 5 or 7, including combinations thereof (and the corresponding modifications to the encoding nucleotides) will produce Angptl4 polypeptide derivatives having functional and chemical characteristics similar to those of naturally occurring Angptl4 polypeptides while minimizing undesirable properties such as LPL inhibitory activity. In contrast, substantial modifications in the functional and/or chemical characteristics of Angptl4 polypeptides may be accomplished by selecting substitutions in the amino acid sequence of any of SEQ ID NOS: 1 or 3 or 5 or 7, including combinations thereof, that differ significantly in their effect on maintaining (a) the structure of the molecular backbone in the area of the substitution.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine.

Conservative amino acid substitutions also encompass non-naturally occurring amino acid residues which are typically incorporated by chemical peptide synthesis rather than by synthesis in biological systems. These include peptidomimetics, and other reversed or inverted forms of amino acid moieties. It will be appreciated by those of skill in the art that nucleic acid and polypeptide molecules described herein may be chemically synthesized as well as produced by recombinant means.

Naturally occurring residues may be divided into classes based on common side chain properties: 1) hydrophobic: norleucine, Met, Ala, Val, Leu, Ile; 2) neutral hydrophilic: Cys, Ser, Thr, Asn, Gln; 3) acidic: Asp, Glu; 4) basic: H is, Lys, Arg; 5) residues that influence chain orientation: Gly, Pro; and 6) aromatic: Trp, Tyr, Phe.

For example, non-conservative substitutions may involve the exchange of a member of one of these classes for a member from another class. Such substituted residues may be introduced into regions of the Angptl4 polypeptide derivatives that are homologous with non-human Angptl4 polypeptide orthologs, or into the non-homologous regions of the molecule.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is understood in the art (Kyte et al., J. Mol. Biol., 157:105-131, 1982). It is known that certain amino acids may be substituted for other amino acids having a similar hydropathic index or score and still retain a similar biological activity.

In making changes based upon the hydropathic index, the substitution of amino acids whose hydropathic indices are within +/−2 may be used; in an alternate embodiment, the hydropathic indices are with +/−1; in yet another alternate embodiment, the hydropathic indices are within +/−0.5.

It is also understood in the art that the substitution of like amino acids can be made effectively on the basis of hydrophilicity. The greatest local average hydrophilicity of a polypeptide as governed by the hydrophilicity of its adjacent amino acids, correlates with a biological property of the protein.

The following hydrophilicity values have been assigned to amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within +/−2 may be used; in an alternate embodiment, the hydrophilicity values are with +/−1; in yet another alternate embodiment, the hydrophilicity values are within +/−0.5.

Desired amino acid substitutions (whether conservative or non-conservative) can be determined by those skilled in the art at the time such substitutions are desired. For example, amino acid substitutions can be used to identify important residues of the Angptl4 polypeptide, or to increase or decrease the affinity of the Angptl4 polypeptide with a particular binding target in order to increase or decrease an Angptl4 polypeptide activity.

Exemplary amino acid substitutions are set forth in Table 3.

TABLE 3

| Original Amino Acid | Exemplary substitution | Preferred substitution |
|---|---|---|
| Ala | Val, Leu, Ile | Val |
| Arg | Lys, Gln, Asn | Lys |
| Asn | Glu | Glu |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Ile, Val, Met, Ala, Phe, Norleucine | Ile |
| Lys | Arg, 1,4-diaminobutyric acid, Gln, Asn | Arg |
| Met | Leu, Phe, Ile | Leu |
| Phe | Leu, Val, Ile, Ala, Tyr | Leu |
| Pro | Ala, Gly | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth in any of SEQ ID NOS: 1 or 3 or 5 or 7, including combinations thereof, using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of an Angptl4 polypeptide to such similar polypeptides. With such a comparison, one can identify residues and portions of the molecules that are conserved among similar polypeptides. It will be appreciated that changes in areas of an Angptl4 polypeptide that are not conserved relative to such similar polypeptides would be less likely to adversely affect the biological activity and/or structure of the Angptl4 polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in an Angptl4 polypeptide that correspond to amino acid residues that are important for activity or structure in similar polypeptides. One skilled in the art may opt for chemically similar amino acid substitutions for such predicted important amino acid residues of an Angptl4 polypeptide.

One skilled in the art can also analyze the three-dimensional structure and amino acid sequence in relation to that structure in similar polypeptides. In view of that information, one skilled in the art may predict the alignment of amino acid residues of an Angptl4 polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test Angptl4 polypeptide derivatives containing a single amino acid substitution at each desired amino acid residue. The derivatives can then be screened using activity assays know to those skilled in the art and as disclosed herein. Such derivatives could be used to gather information about suitable substitution. For example, if one discovered that a change to a particular amino acid residue resulted in destroyed, undesirably reduced, or unsuitable activity, derivatives with such a change would be avoided. In other words, based on information gathered from such routine experiments, one skilled in the art can readily determine the amino acids where further substitutions should be avoided either alone or in combination with other mutations.

Numerous scientific publications have been devoted to the prediction of secondary structure from analyses of amino acid sequences (see Chou et al., Biochemistry, 13(2):222-245, 1974; Chou et al., Biochemistry, 113(2):211-222, 1974; Chou et al., Adv. Enzymol. Relat. Areas Mol. Biol., 47:45-148, 1978; Chou et al., Ann. Rev. Biochem., 47:251-276, 1979; and Chou et al., Biophys. J., 26:367-384, 1979). Moreover, computer programs are currently available to assist with predicting secondary structure of polypeptides. Examples include those programs based upon the Jameson-Wolf analysis (Jameson et al., Comput. Appl. Biosci., 4(1): 181-186, 1998; and Wolf et al., Comput. Appl. Biosci., 4(1):187-191; 1988), the program PepPlot®. (Brutlag et al., CABS, 6:237-245, 1990; and Weinberger et al., Science, 228:740-742, 1985), and other new programs for protein tertiary structure prediction (Fetrow. et al., Biotechnology, 11:479-483, 1993).

Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure (see Holm et al., Nucl. Acid. Res., 27(1):244-247, 1999).

Additional methods of predicting secondary structure include "threading" (Jones, D., Curr. Opin. Struct. Biol., 7(3):377-87, 1997; Suppl et al., Structure, 4(1):15-9, 1996), "profile analysis" (Bowie et al., Science, 253:164-170, 1991; Gribskov et al., Meth. Enzym., 183:146-159, 1990; and Gribskov et al., Proc. Nat. Acad. Sci., 84(13): 4355-4358, 1987), and "evolutionary linkage" (See Home, supra, and Brenner, supra).

Any of the polypeptide forms discussed herein may also contain a sequence useful in the identification or purification of the polypeptide; an example of such a sequence is the C-terminal V5 tag. The foregoing also includes nucleic acid sequences (such as, but not limited to cDNA sequences) coding for such polypeptides, including polypeptide derivatives as described herein.

Compositions

Useful compositions of the present disclosure may comprise one or more polypeptides of the present disclosure useful in the treatment and prevention methods of the present disclosure; useful compositions also include one or more nucleic acids coding for one or more polypeptides of the present disclosure useful in the treatment and prevention methods of the present disclosure. The compositions disclosed may comprise one or more of such compounds, in combination with a pharmaceutically acceptable carrier. Examples of such carriers and methods of formulation may be found in Remington: The Science and Practice of Pharmacy (20$^{th}$ Ed., Lippincott, Williams & Wilkins, Daniel Limmer, editor). To form a pharmaceutically acceptable composition suitable for administration, such compositions will contain an therapeutically effective amount of compound.

The pharmaceutical compositions of the disclosure may be used in the treatment and prevention methods of the present disclosure. Such compositions are administered to a subject in amounts sufficient to deliver a therapeutically effective amount of the compound(s) so as to be effective in the treatment and prevention methods disclosed herein. The therapeutically effective amount may vary according to a variety of factors such as, but not limited to, the subject's condition, weight, sex and age. Other factors include the mode and site of administration. The pharmaceutical compositions may be provided to the subject in any method known in the art. Exemplary routes of administration include, but are not limited to, subcutaneous, intravenous, topical, epicutaneous, oral, intraosseous, and intramuscular. The compositions of the present disclosure may be administered only one time to the subject or more than one time to the subject. Furthermore, when the compositions are administered to the subject more than once, a variety of regimens may be used, such as, but not limited to, one per day, once per week or once per month. The compositions may also be administered to the subject more than one time per day. The therapeutically effective amount and appropriate dosing regimens may be identified by routine testing in order to obtain optimal activity, while minimizing any potential side effects. In addition, co-administration or sequential administration of other agents may be desirable.

The compositions of the present disclosure may be administered systemically, such as by intravenous administration, or locally such as by subcutaneous injection or by application of a paste or cream.

In one embodiment, a nucleic acid, which may be in the form of a suitable plasmid or vector, is provided that codes for an Angptl4 polypeptide or Angptl4 polypeptide variant of the present disclosure. Such nucleic acid is introduced into a cell, which may be obtained from the subject, by suitable methods known in the art (for example, electroporation). In one embodiment, the cell is an adipose cell. The cells may be assayed for expression of the Angptl4 polypeptide or polypeptide derivative (in one embodiment, expression of the polypeptide can be determined by the presence of a tag on the polypeptide as discussed herein). The cells expressing an Angptl4 polypeptide of polypeptide derivative may then be introduced into the subject. In one embodiment, the cells are administered to the subject by subcutaneous injection; other methods of administration may also be used, including those discussed herein. The cells then express Angptl4 polypeptide or an Angptl4 polypeptide derivative, which is taken up into the circulation.

The compositions of the present disclosure may further comprise agents which improve the solubility, half-life, absorption, etc. of the compound(s). Furthermore, the compositions of the present disclosure may further comprise agents that attenuate undesirable side effects and/or or decrease the toxicity of the compounds(s). Examples of such agents are described in a variety of texts, such a, but not limited to, Remington: The Science and Practice of Pharmacy (20$^{th}$ Ed., Lippincott, Williams & Wilkins, Daniel Limmer, editor).

The compositions of the present disclosure can be administered in a wide variety of dosage forms for administration. For example, the compositions can be administered in forms, such as, but not limited to, tablets, capsules, sachets, lozenges, troches, pills, powders, granules, elixirs, tinctures, solutions, suspensions, elixirs, syrups, ointments, creams, pastes, emulsions, or solutions for intravenous administration or injection. Other dosage forms include administration transdermally, via patch mechanism or ointment. Any of the foregoing may be modified to provide for timed release and/or sustained release formulations.

In the present disclosure, the pharmaceutical compositions may further comprise a pharmaceutically acceptable carriers include, but are not limited to, vehicles, adjuvants, surfactants, suspending agents, emulsifying agents, inert fillers, diluents, excipients, wetting agents, binders, lubricants, buffering agents, disintegrating agents and carriers, as well as accessory agents, such as, but not limited to, coloring agents and flavoring agents (collectively referred to herein as a carrier). Typically, the pharmaceutically acceptable carrier is chemically inert to the active compounds and has no detrimental side effects or toxicity under the conditions of use. The pharmaceutically acceptable carriers can include polymers and polymer matrices. The nature of the pharmaceutically acceptable carrier may differ depending on the particular dosage form employed and other characteristics of the composition.

For instance, for oral administration in solid form, such as but not limited to, tablets, capsules, sachets, lozenges, troches, pills, powders, or granules, the compound(s) may be combined with an oral, non-toxic pharmaceutically acceptable inert carrier, such as, but not limited to, inert fillers, suitable binders, lubricants, disintegrating agents and accessory agents. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, and the like. Disintegrators include, without limitation, starch, methyl cellulose, agar, bentonite, xanthum gum and the like. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid as well as the other carriers described herein. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

For oral liquid forms, such as but not limited to, tinctures, solutions, suspensions, elixirs, syrups, the nucleic acid molecules of the present disclosure can be dissolved in diluents, such as water, saline, or alcohols. Furthermore, the oral liquid forms may comprise suitably flavored suspending or dispersing agents such as the synthetic and natural gums, for example, tragacanth, acacia, methylcellulose and the like. Moreover, when desired or necessary, suitable and coloring agents or other accessory agents can also be incorporated into the mixture. Other dispersing agents that may be employed include glycerin and the like.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The compound(s) may be administered in a physiologically acceptable diluent, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as, but not limited to, a soap, an oil or a detergent, suspending agent, such as, but not limited to, pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include polyethylene sorbitan fatty acid esters, such as sorbitan monooleate and the high molecular weight adducts of ethylene oxide with a hydrophobic base, formed by the condensation of propylene oxide with propylene glycol, oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkylbeta-aminopropionates, and 2-alkylimidazoline quaternary ammonium salts, and (e) mixtures thereof.

Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight.

Topical dosage forms, such as, but not limited to, ointments, creams, pastes, emulsions, containing the nucleic acid molecule of the present disclosure, can be admixed with a variety of carrier materials well known in the art, such as, e.g., alcohols, aloe vera gel, allantoin, glycerine, vitamin A and E oils, mineral oil, PPG2 myristyl propionate, and the like, to form alcoholic solutions, topical cleansers, cleansing creams, skin gels, skin lotions, and shampoos in cream or gel formulations. Inclusion of a skin exfoliant or dermal abrasive preparation may also be used. Such topical preparations may be applied to a patch, bandage or dressing for transdermal delivery or may be applied to a bandage or dressing for delivery directly to the site of a wound or cutaneous injury.

The compound(s) of the present disclosure can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. Such liposomes may also contain monoclonal antibodies to direct delivery of the liposome to a particular cell type or group of cell types.

The compound(s) of the present disclosure may also be coupled with soluble polymers as targetable drug carriers. Such polymers can include, but are not limited to, polyvinylpyrrolidone, pyran copolymer, polyhydroxypropylmethacryl-amidephenol, polyhydroxyethylaspartamidephenol, or polyethyl-eneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Results

In the following results, the methods used were those methods specified in the Methods section of the present disclosure and the references cited therein. Some of the following results are described in Clement L C et. al., Podocyte secreted Angiopoietin-like 4 mediates proteinuria in glucocorticoid-sensitive nephrotic syndrome, Nature Medicine, January 2011 (this reference is hereby incorporated by reference for the disclosure contained therein regarding the use of Angptl4 polypeptides).

Patients with Nephrotic Syndrome have Increased Levels of Circulating Angptl4

Patients with Nephrotic syndrome have increased circulating levels of Angptl4 polypeptide. 200 μg human plasma from patients (n=4 patients/group) with diagnosed with MCD and MN and patients in MCD relapse were analyzed by 2D gel electrophoresis and Western blots were prepared using anti-Angptl4 antibodies (FIG. 1A). FIG. 1A shows that only patients with MCD relapse and MN had increased levels of Angptl4 (indicated by arrows). This form of Angptl4 exists as a neutral pI form and is present as monomers and oligomers.

aP2-Angptl4 TG Rats have Increased Circulating Levels of Angptl4

Figure 1B:
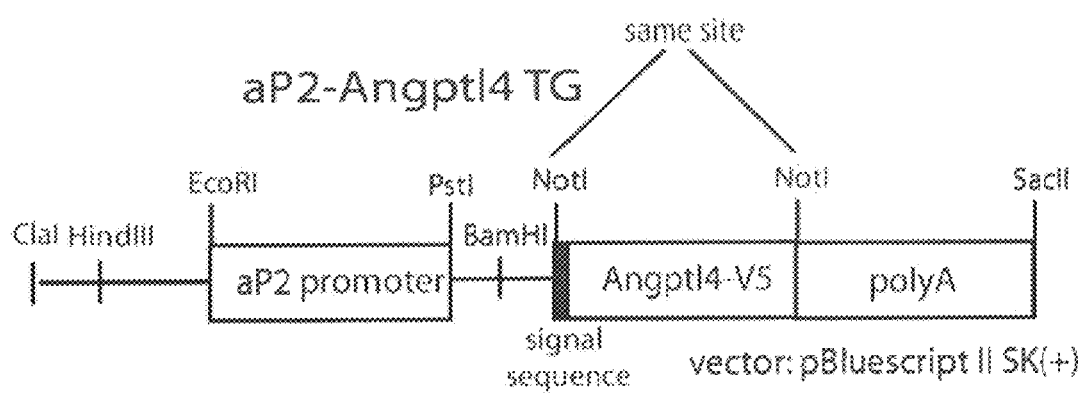
FIG. 1B shows a transgenic (TG) rat model for adipose tissue specific over expression of Angptl4 (aP2-Angplt4 TG).
Figure 1C:
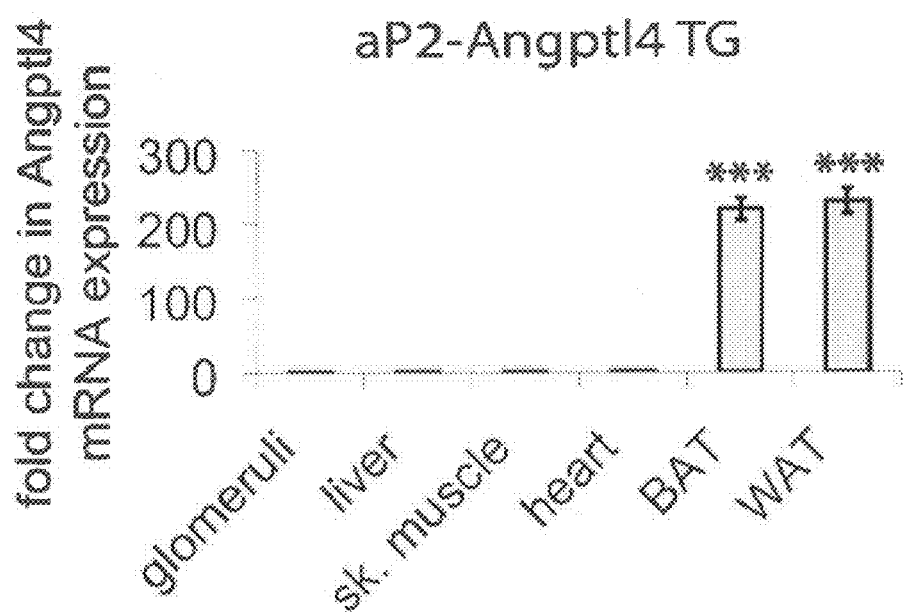
FIG. 1C shows tissue specific over expression of Angptl4 mRNA (n=3 rats/group) in aP2-Angptl4 TG rats. WAT is white adipose tissue, BAT is brown adipose tissue. ***P<0.001.

A transgenic rat models for adipocyte specific Angptl4 overexpression was developed and is shown in FIG. 1B (aP2-Angptl4 TG). Analysis of mRNA expression in organs that normally express Angptl4 confirmed specificity of expression, with Angplt4 being detected in brown adipose tissue (BAT) and white adipose tissue (WAT) (FIG. 1C).

Figure 1D:
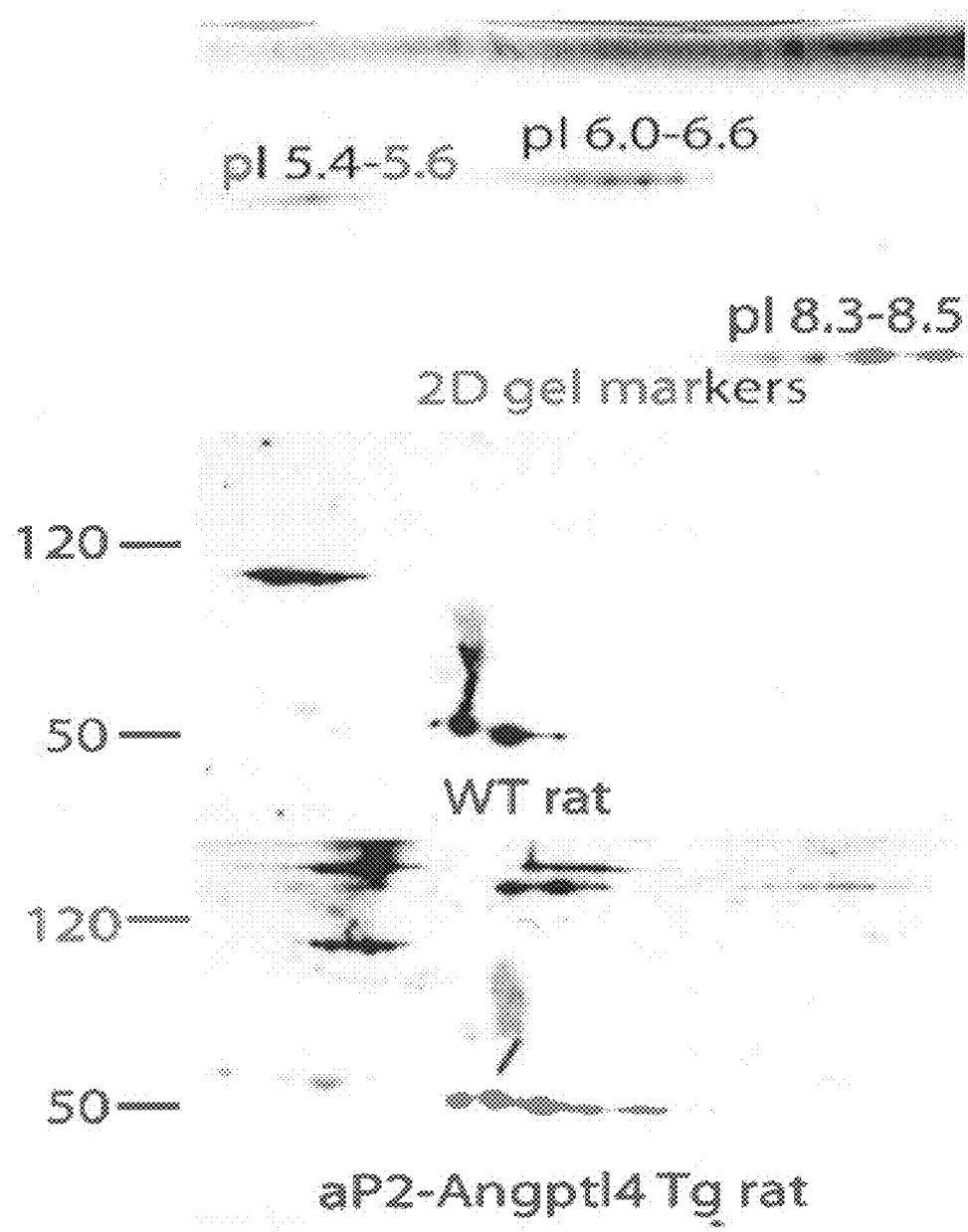
FIG. 1D shows 2D gel electrophoresis of 200 μg plasma, followed by Western blot for Angptl4 and demonstrates that heterozygous aP2-Angptl4 TG rats had higher circulating Angptl4 levels than wild type rats (age 3 months, n=3 blots/group).
Figure 1E:
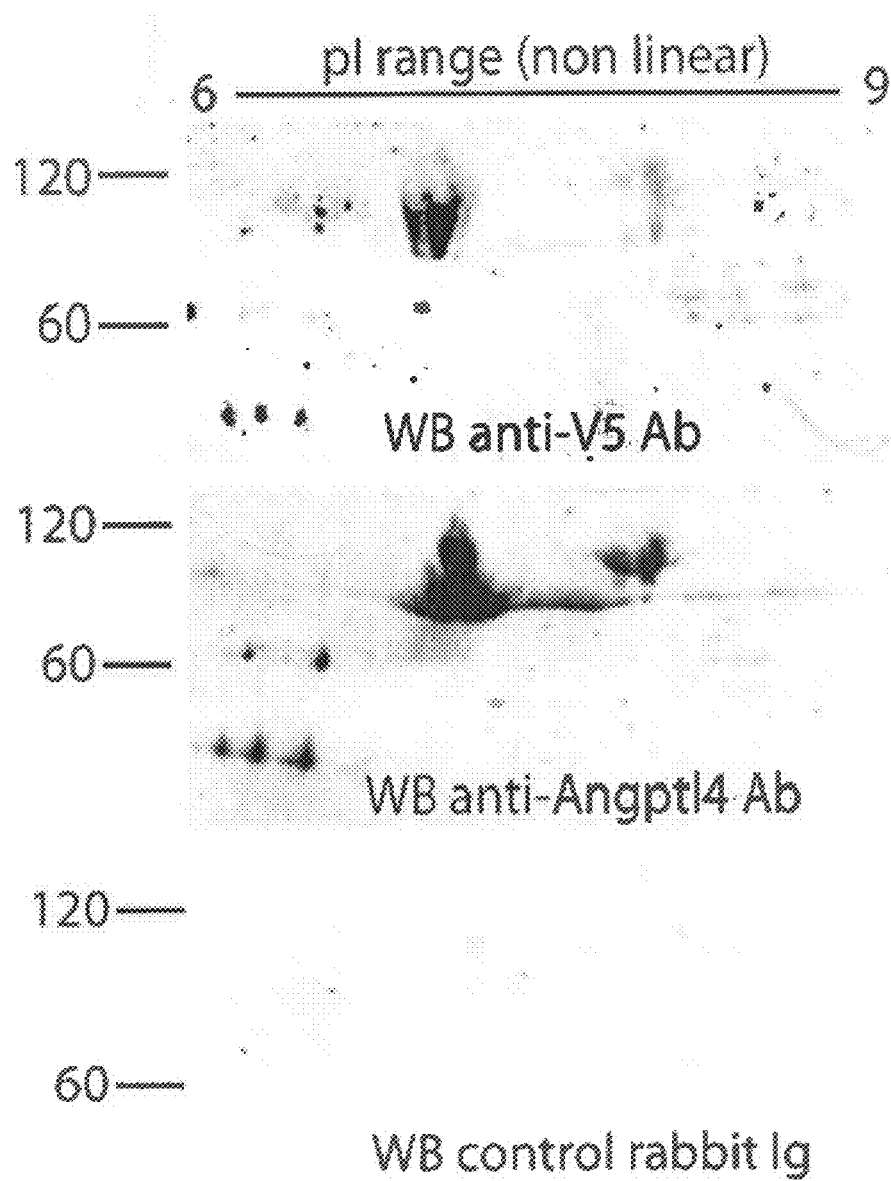
FIG. 1E shows 2D gel electrophoresis of 200 μg plasma, followed by Western blot with the anti-V5 and anti-Angptl4 antibodies and demonstrates the presence of adipose tissue secreted V5-tagged Angptl4 in the plasma of aP2-Angptl4 TG rats.
Figure 1F:
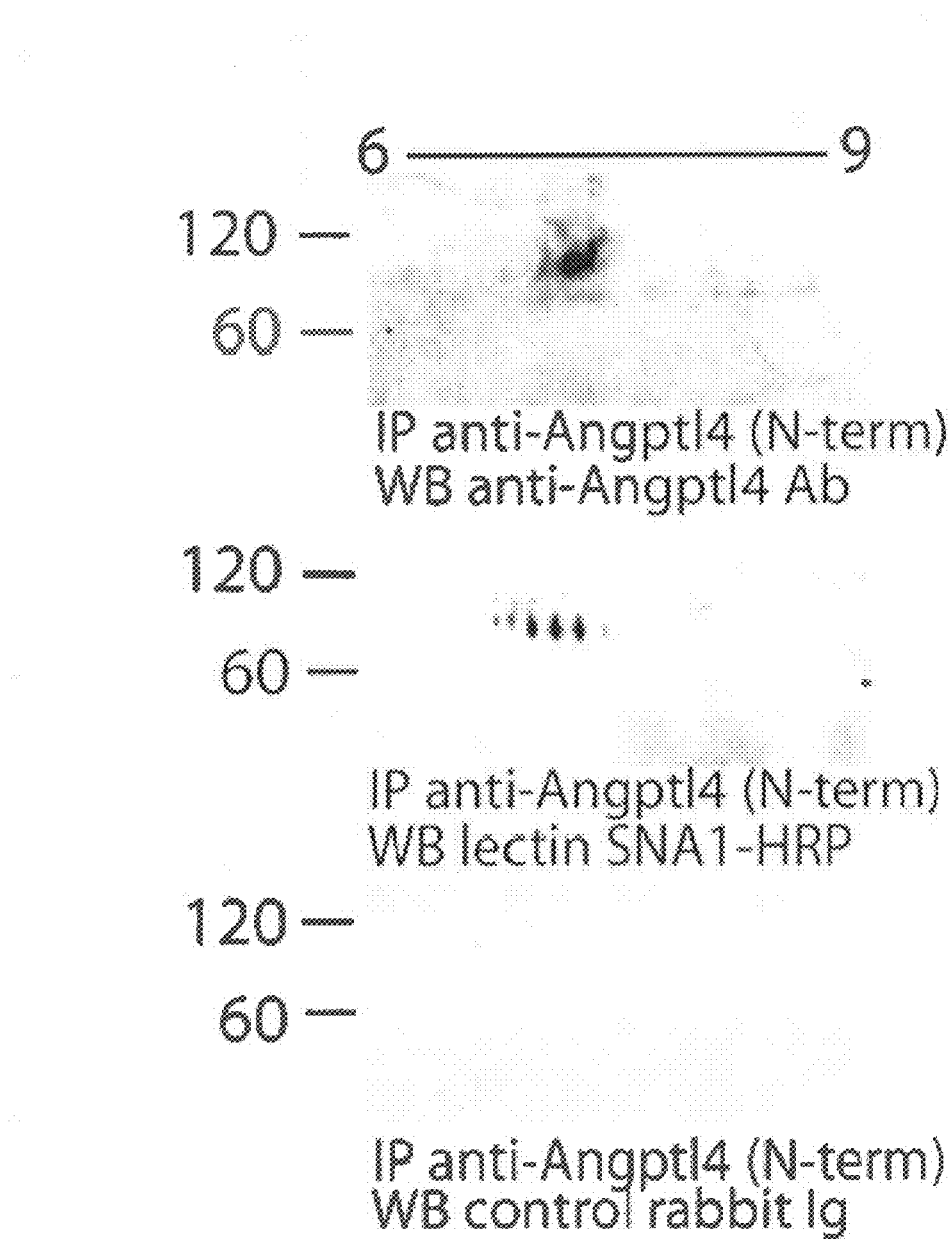
FIG. 1F shows 2D gel electrophoresis of anti-N-terminal Angptl4 immunoprecipitates from aP2-Angptl4 TG rat plasma followed by Western blotting using lectin SNA I and anti-Angptl4 antibodies and confirmed the presence of circulating sialylated Angptl4 in the aP2-Angptl4.

2D gel electrophoresis of 200 μg plasma, followed by Western blotting using an anti-Angptl4 antibody revealed that heterozygous aP2-Angptl4 TG rats had higher circulating Angptl4 levels than wild type rats (FIG. 1D) (age 3 months, n=3 blots/group). FIG. 1E shows 2D gel electrophoresis of 200 μg plasma, followed by Western blotting using anti-Angptl4 and anti-V5 antibodies show the presence of adipose tissue secreted V5-tagged Angptl4 in the plasma of aP2-Angptl4 TG rats. 2D gel electrophoresis of immunoprecipitated Angptl4 from aP2-Angptl4 TG rat plasma (using an antibody specific for the N-terminus of Angptl4), followed by Western blotting using anti-Angptl4 or anti-lectin. SNA I antibodies revealed the presence of sialylated Angptl4 polypeptide in the circulation.

Figure 1G:
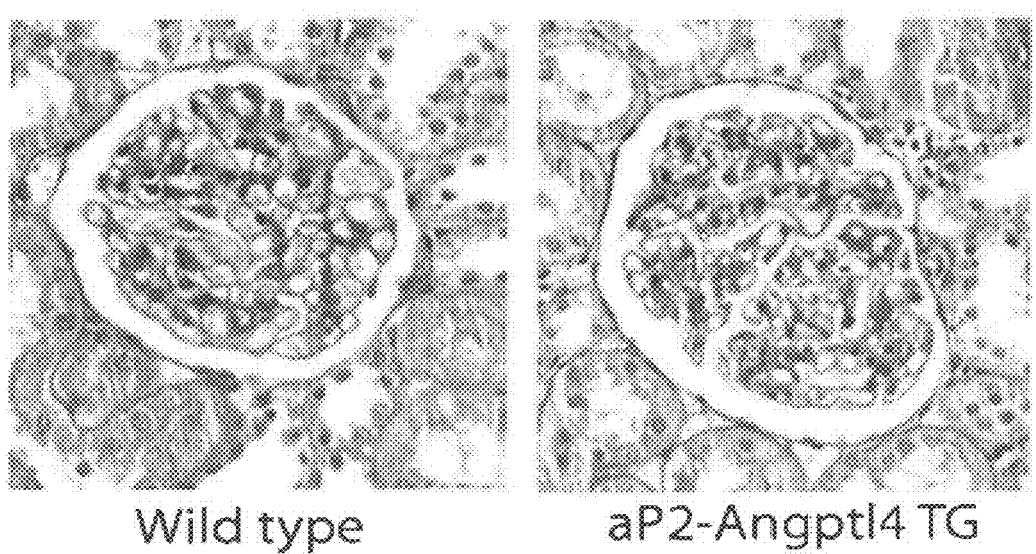
FIG. 1G shows PAS stained sections from 3 month old heterozygous aP2-Angptl4 TG rats (n=3 rats/group) and demonstrates normal glomerular morphology (magnification 400×).
Figure 1H:
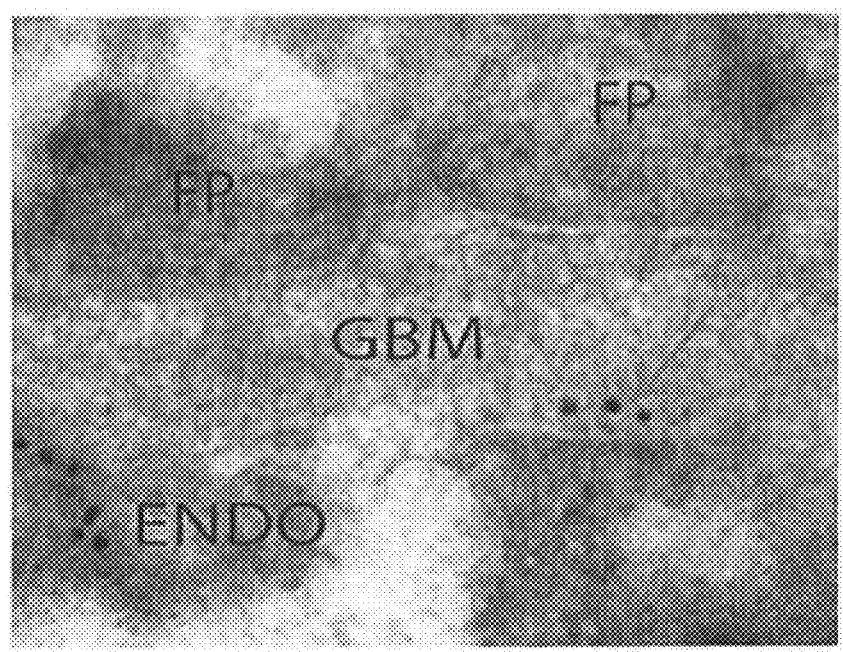
FIG. 1H shows immunogold EM with anti-V5 antibody to specifically detect transgenic protein in 3 month heterozygous aP2-Angplt4 TG male rats and demonstrated gold particles selectively on the endothelial surface in aP2-Angptl4 TG rats (indicated by arrows).

The aP2-Angptl4 TG rats had morphologically normal glomeruli by light (FIG. 1G) and electron microscopy (not shown), and glomerular Angptl4 expression was unchanged. This is in contrast to podocyte specific expression of Angptl4, where such expression resulted in glomerular defects, including progressive development of foot process effacement between age one to five months (see U.S. Provisional application No. 61/351,865 (filed 5 Jun. 2010), which is hereby incorproated by reference for such teaching).

Immunogold EM using anti-V5 antibody to specifically detect transgene expressed protein in 3 month old heterozygous aP2-Angptl4 TG male rats demonstrated detection selectively on the endothelial surface, indicating that circulating Angptl4 middle and high order oligomers do not enter the GBM and have receptors on the endothelial surface. The effects of circulating Angptl4 is relevant to both human and experimental nephrotic syndrome, since adipose tissue upregulation of Angptl4 is noted in later stages of nephrotic syndrome, when proteinuria is on the decline.

Figure 2A:
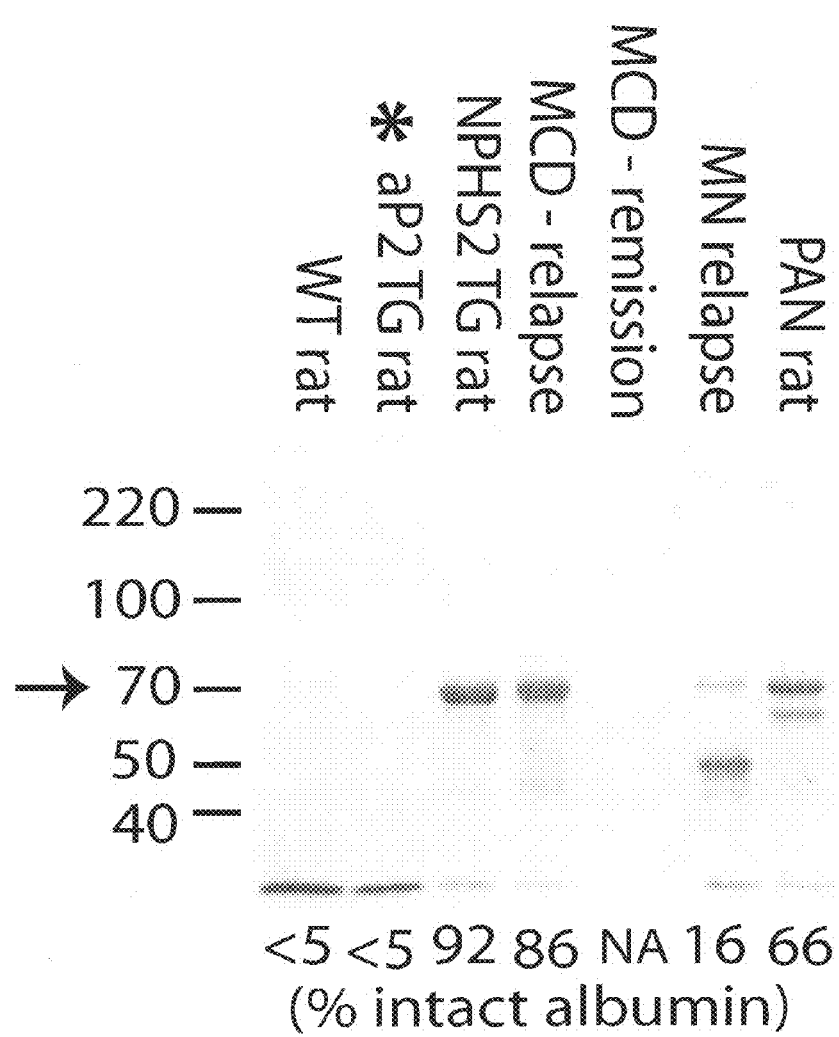
FIG. 2A shows assessment of urinary protein excretion (3 μg/lane, except MCD remission) in different human and experimental disease conditions by GelCode blue stained SDS PAGE and demonstrated the absence of significant proteinuria in aP2-Angptl4 TG rats (lane marked with *, arrow shows intact albumin at around 70 kDa).
Figure 2B:
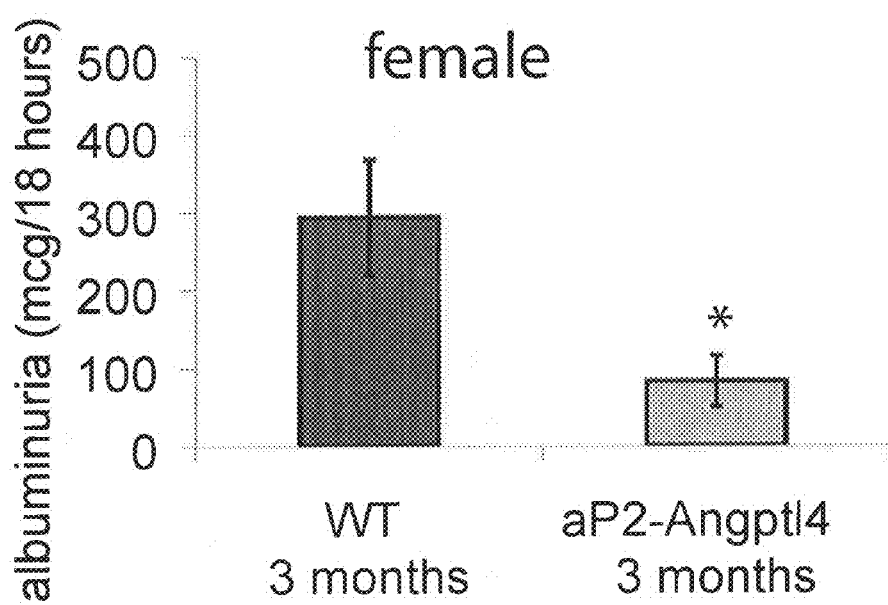
FIG. 2B shows assessment of albuminuria by ELISA and revealed that heterozygous female aP2-Angptl4 TG rats had lower albuminuria than wild type littermates (n=6 rats/group).
Figure 2C:
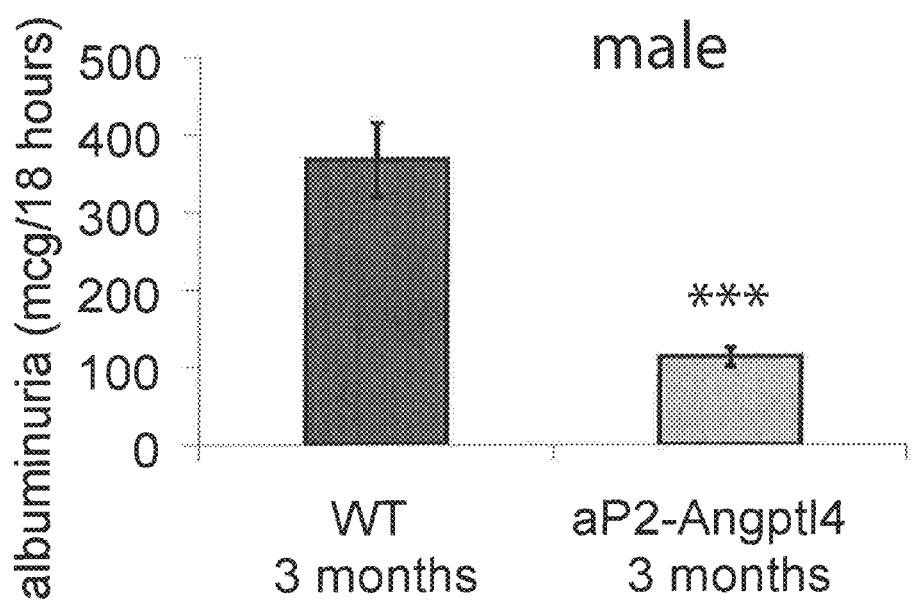
FIG. 2C shows assessment of albuminuria by ELISA and revealed that heterozygous male aP2-Angplt4 TG rats had lower albuminuria than wild type littermates (n=6 rats/group).
Figure 2D:
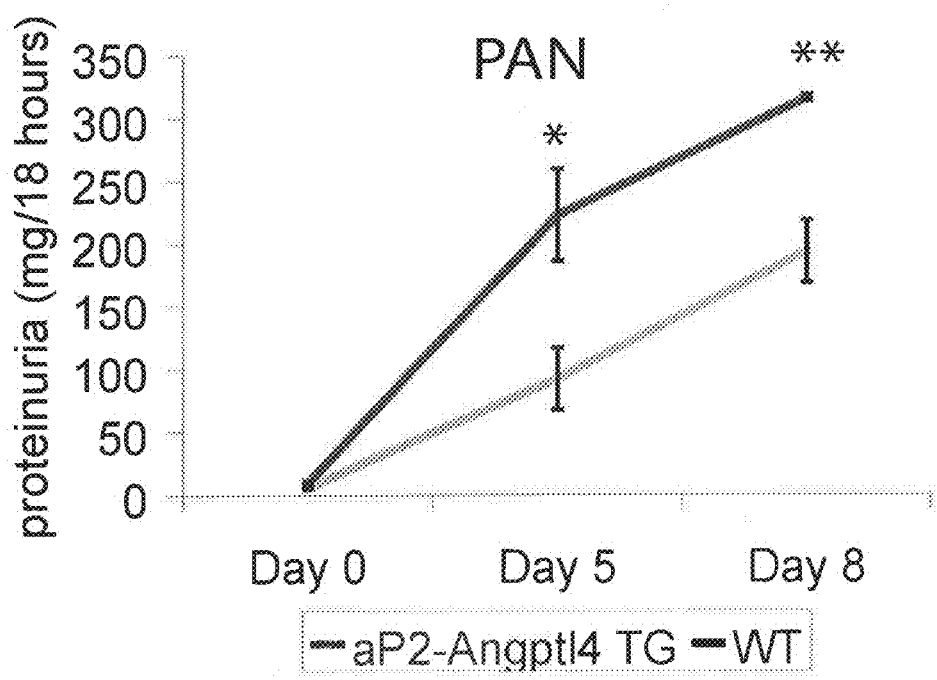
FIG. 2D shows induction of puromycin nephrosis (PAN), a model of nephrotic syndrome, in wild type and aP2-Angptl4 TG rats and demonstrates less proteinuria in aP2-Angptl4 TG rats compared to wild type littermates (n=8 rats/group). $*P<0.05$, $P<0.01$ compared to corresponding controls
Figure 2E:
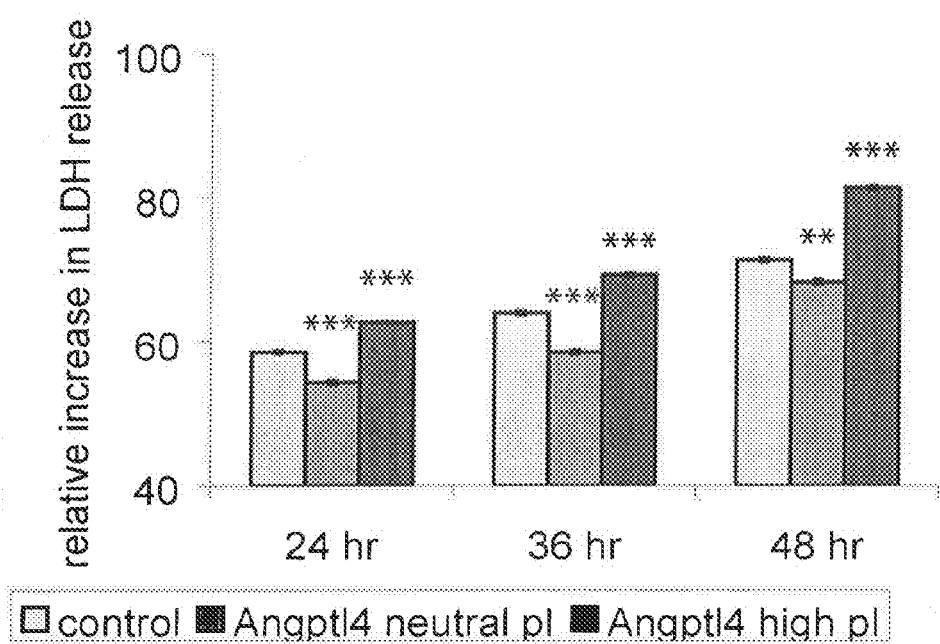
FIG. 2E shows recombinant Angptl4 had protective effects on cultured glomerular endothelial cells (GEnCs). $P<0.01$, $*P<0.001$ compared to corresponding controls

Relationship of Increased Circulating Levels of Angptl4 with Proteinuria and Albuminuria To examine the relationship between circulating levels of Angptl4 proteinuria, including albuminuria, proteinuria was analyzed in aP2-Angptl4 TG rats. FIG. 2A shows that that aP2-Angptl4 TG do not exhibit proteinuria as determined by analysis of urinary proteins. In FIG. 2A urinary proteins were analyzed by GelCode blue stained SDS PAGE (3 μg/lane, except MCD remission) (densitometry readings are provided under each lane). The intact albumin band is observed at 70 kDa (indicated by arrow). As can be seen, WT rats, aP2-Angptl4 TG rats and MCD patients in remission showed little or no intact albumin in the analysed urinary samples, wherein podocin (NPHS2)-Angplt4 TG rats (a rat transgenic model having podocytes specific Angptl4 expression and shown to develop MCD with proteinuria; see U.S. Provisional application No. 61/351,865, which is hereby incorporated by reference for such teaching), MCD relapse, MN relapse and PAN rats (a rat model of nephrotic syndrome) showed strong albumin staining indicative of albuminuria. FIG. 2B shows that female heterozygous aP2-Angptl4 female TG rats had decreased albuminuria as compared to WT littermate controls. FIG. 2C shows the same results for aP2-Angptl4 heterozygous male TG rats. FIG. 2D shows that aP2-Angptl4 TG rats exhibited reduced proteinuria in the puromycin nephrosis (PAN model; a rat model of nephrotic syndrome) as compared to WT littermates. As demonstrated above, aP2-Angptl4 TG rats have higher circulating Angptl4 levels that migrate at or around neutral isoelectric point, and is sialylated. These results show a role for circulating Angptl4 in reducing proteinuria and nephrotic syndrome.

Since endothelial binding of adipose tissue secreted Angptl4 bound to glomerular endothelium, experiments were conducted to determine the effect of recombinant Angptl4 on glomerular epithelial cells (GEnCs) to investigate whether lower baseline albuminuria and less PAN induced proteinuria in this rat model were mediated by glomerular endothelial protection. GEnCs were subject to oxidative injury by addition of hydrogen peroxide and into the culture media and incubated with concentrated supernatant (600 μg/well) from the control stable cell line, Angptl4-HEK293 cell line (secreting high isoelectric point (pI), hyposialylated Angptl4) or Angptl4-HEK293 cell line incubated with ManNAc (neutral pI, normally sialylated Angptl4). It should be noted that the high pI form of Angptl4 is secreted in large amounts from podocytes in MCD. Release of LDH was assessed as a marker of cell injury. Control cells without hydrogen peroxide injury were given a relative score of 1. High pI Angptl4 increased GEnC injury, whereas neutral pI Angptl4 (which comprises most of circulating Angptl4) was significantly protective at all measured time points. (n=3 readings/condition).

Figure 2F:
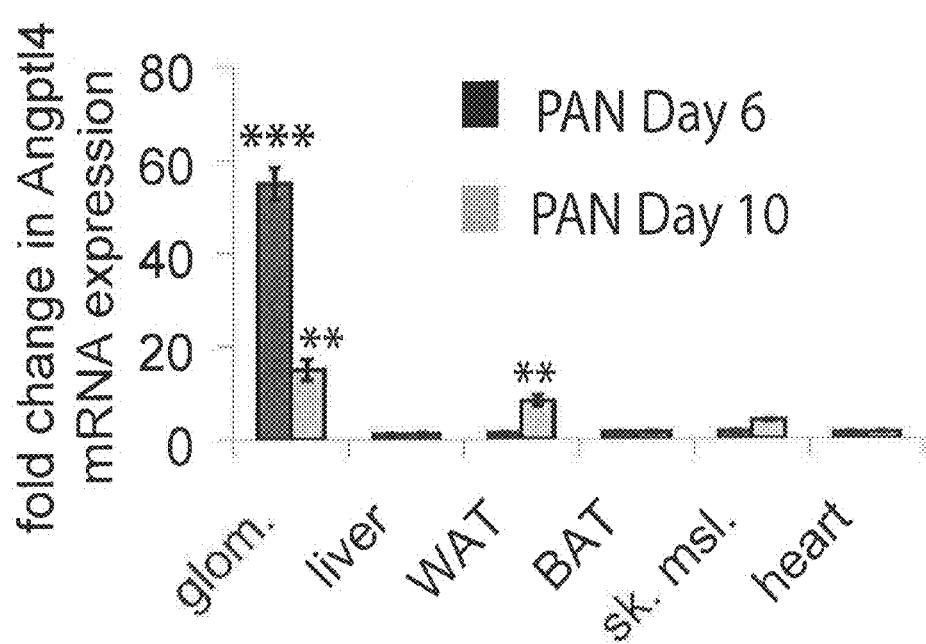
FIG. 2F shows upregulation of Angptl4 in wild type rats in disease models like PAN on Day 6 was exclusively glomerular, while upregulation of Angptl4 in adipose tissue was noted on Day 10 when proteinuria and glomerular Angptl4 expression are on the decline (n=3 rats/sample). $P<0.01$, $***P<0.001$ compared to corresponding controls
Figure 2G:
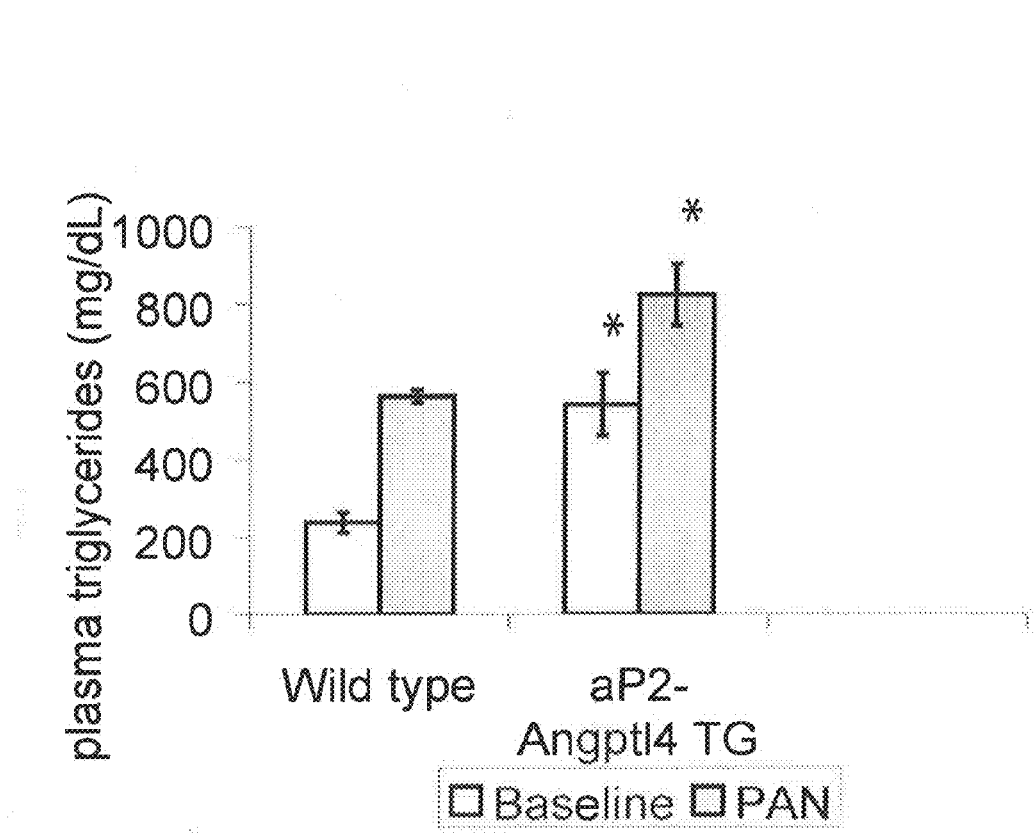
FIG. 2G shows increased circulating levels of Angptl4 at baseline and after induction of PAN in aP2-Angptl4 TG rats results in increased plasma triglyceride levels compared to wild type rats. $*P<0.05$ compared to corresponding controls
Figure 2H:
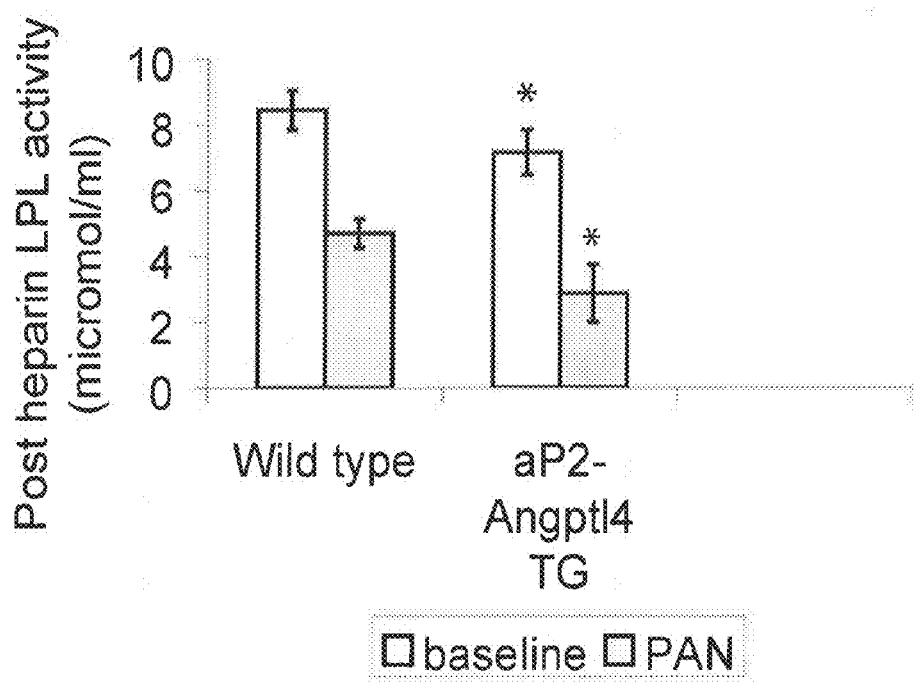
FIG. 2H shows increased circulating levels of Angptl4 at baseline and after induction of PAN in aP2-Angptl4 TG rats results in reduced post-heparin lipoprotein lipase (LPL) activity compared to wild type rats. $*P<0.05$ compared to corresponding controls FIG. 3 show the primers and probes used for Taqman real time PCR (SEQ ID NOS. 11-22).

Upregulation of Angptl4 in wild type rats on PAN Day 6 was exclusively glomerular, whereas upregulation in adipose tissue was noted on Day 10 when proteinuria and glomerular Angptl4 expression are on the decline (n=3 rats/sample) (FIG. 2F). Therefore, increases in circulating Angptl4 levels are coincident with the protective effect of circulating Angptl4 in nephrotic syndrome and reduction of proteinuria. The effects of circulating Angptl4 are likely to be relevant to both human and experimental MCD, since adipose tissue upregulation of Angptl4 is noted in later stages of PAN when proteinuria is on the decline. Furthermore, increased circulating Angptl4 levels at baseline and after induction of PAN in aP2-Angptl4 TG rats resulted in increased plasma triglyceride levels (FIG. 2G) and reduced post-heparin lipoprotein lipase activity (FIG. 2H) as compared to wild type rat.

Figure 4:
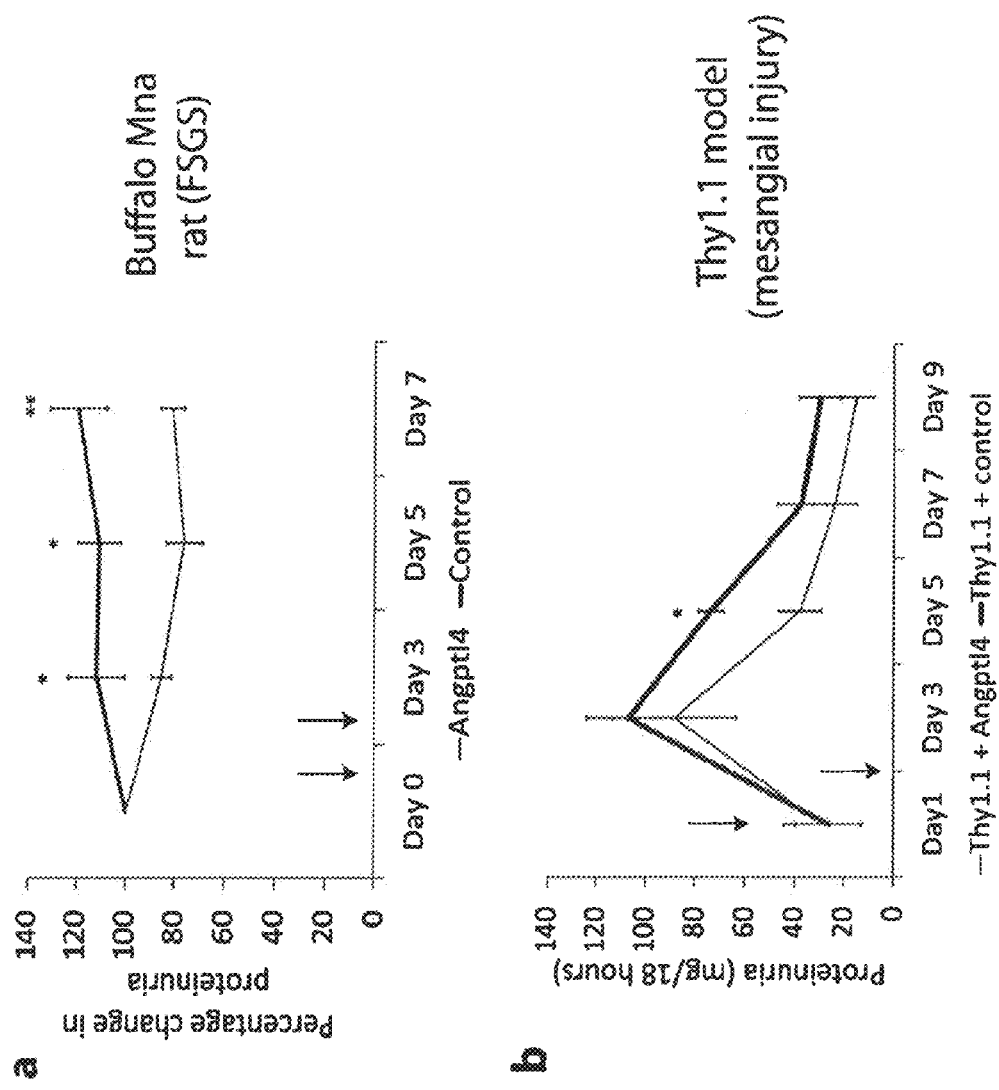
FIG. 4 shows recombinant Angptl4 reduces proteinuria in animal models of human glomerular disease.

In order to demonstrate the effectiveness of the therapeutic delivery of Angptl4 into the circulation, wild type Angptl4 or a control protein was administered to Buffalo/Mna rats, a model of FSGS, or to Wistar rats in which Thy1.1 nephritis, a short term model of mesangial injury, was induced (FIGS. 4A and B). Wild-type recombinant Angptl4 polypeptide was generated by harvesting of recombinant protein. Angptl4-HEK293 stable or pcDNA3.1-HEK293 control stable cell lines were grown to confluence in 15 cm dishes, washed twice with warm PBS, and incubated with serum free DMEM without Phenol Red, with or without 25 mM ManNAc, for 48 hours. Cells were harvested and the supernatant concentrated. Concentrated supernatant from one 15 cm dish was used at each injection time point.

Buffalo/Mna rats spontaneously develop lesions mimicking human FSGS at around age 2 months, including focal and segmental lesions on light microscopy, effacement of podocyte foot processes on electron microscopy, and proteinuria. The rats develop progressive increase in proteinuria as they age. The rats used in the above studies were male and 5 months old. Anti-Thy1.1 nephritis was induced by injection of 150 μg of anti-Thy1.1 (Ox-7 hybridoma) or control IgG IV into different groups of male Wistar rats (100-125 gm, n=4 rats/group).

In the Buffalo/Mna rat model, assessment of baseline proteinuria was made on Day 0. Angptl4 or control protein were injected intra-peritoneally on two consecutive days (Days 1 & 2, arrows) into Buffalo Mna rats (n=4 rats/group). Proteinuria was assessed on alternate days, and expressed as a percentage of baseline values. Significant reduction in proteinuria was noted in recombinant Angptl4 treated rats.

In the Thy1.1 nephritis model, proteinuria confirmed on Day 1. Rats were injected intravenously with either recombinant Angptl4 or control protein on two consecutive days (Days 1 & 2, arrows). Proteinuria was then assessed. As shown in FIG. 4B, proteinuria was lower in Angptl4 treated rats throughout, and was statistically significant on Day 5.

These results show that therapeutic delivery of Angptl4 into the circulation are an effective treatment for nephrotic syndrome, such as but not limited to minimal change disease, focal segmental glomerulosclerosis, membranous nephropathy/membranous glomerulonephritis, membranoproliferative glomerulonephritis or a diabetic condition, such as, but not limited to, diabetic nephropathy, diabetes mellitus, lupus nephritis or primary glomerular disease. Furthermore, these results show that therapeutic delivery of Angptl4 into the circulation are an effective treatment for and conditions related to nephrotic syndrome, such as but not limited to, proteinuria, hypercholesterolemia, hypertriglyceridemia and edema. In one embodiment, the Angptl4 polypeptide is a derivative with decreased LPL inhibitory activity, resistance to cleavage or a derivative described herein. Administration of such a derivative would retain the beneficial effects of Angptl4 treatment without the negative effects associated with inhibition of LPL activity, such as increased plasma triglyceride levels.

Methods

Cloning of Full Length Rat Angptl4, and Generation of Antibody Against Full Length Recombinant Angptl4

The full length rat Angptl4 open reading frame of 1218 bp from our previous experiments (7), excluding the stop codon, was cloned into pcDNA3.1/V5-HisB for eukaryotic expression, and into pET28a for prokaryotic expression. The *E. Coli* expressed purified full length protein was used to generate a polyclonal antibody in rabbits (Proteintech group, Inc. Chicago Ill. USA) that was tested by ELISA and Western blot. Antibody reactive bands were excised from GelCode blue stained gels, trypsin digested and presence of Angptl4 peptide sequences confirmed by MALDI-TOF/TOF. Part of the antiserum was affinity purified to the antigen. Unless otherwise specified, all studies described used this antibody. An additional polyclonal antibody against the N-terminal part of rat Angptl4 (amino acids 7-86 excluding signal peptide) was similarly raised in rabbits.

Induction of Proteinuria in Animal Models of Human Glomerular Disease

All animal studies were approved by the institutional IACUC. Induction of animal models of proteinuria (n=4 rats/group) in WT rats are described in previous publications in parenthesis: PAN (7), PHN (7), PAN with glucocorticoids (20), non-HIV collapsing glomerulopathy (18), nephrotoxic serum induced heterologous phase proteinuria (7). Anti-Thy1.1 nephritis was induced by injection of 200 mcg of anti-Thy1.1 (Ox-7 hybridoma) or control IgG IV into different groups of male Wistar rats (100-125 gm, n=4 rats/group), and rats euthanized after 24 and 72 hours.

The following techniques are described in prior publications: Taqman real time PCR (26), confocal imaging (7), in situ hybridization (27), immunogold EM (26), glomerular extraction and processing for Western blot (26), assessment of charge by PEI method (28). For alcian blue staining, the pH of the staining solution was adjusted to 2.5 using acetic acid, and 0.1% nuclear fast red solution was used as a counterstain. Densitometry of glomerular basement membrane alcian blue stain (20 glomeruli/rat, 3 rats/group) was assessed using Image-Pro software (Media Cybernetics, Inc., Bethesda Md., USA). Densitometry of 2D gel Western blots was assessed using Gel-Pro Analyzer software (Media Cybernetics, Inc.). Taqman real time PCR primers and probes are listed in FIG. 3. For in situ hybridization, the digoxigenin labeled probe for rat Angptl4 included by 1 to 548 of the ORF.

To obtain samples for post heparin LPL activity, rats were injected intravenously with 10 units/100 gm weight of porcine heparin 15 minutes prior to euthanasia, and activity measured using an assay from Roar Biomedical, Inc (New York N.Y.). Serum triglycerides were measured in the fasting state.

Injection of NTS into Angptl4−/− Mice

Angptl4−/− mice were provided to Sander Kersten as a kind gift from Eli Lily Corporation (Indianapolis Ind. USA). The study protocol was approved by the Animal Studies Committee at Wageningen University. Eleven week old male Angptl4−/− or +/+ mice (n=4 mice/group) were injected intravenously with 1.5 mg γ2-nephrotoxic serum (γ2-NTS) or normal sheep serum (Sigma Aldrich St. Louis Mo. USA), spot urine samples collected at 48 hours, mice euthanized at 72 hours, plasma collected for biochemical measurements, and kidneys preserved for histological analysis. Urine albumin was assessed by ELISA (Bethyl laboratories, Montgomery Tex. USA) and urine creatinine measured by mass spectrometry. To assess for foot process effacement, the mean width of foot processes was first measured in control treated Angptl4+/+ mouse transmission electron micrographs (10 equally spaced readings/loop, 3 loops/glomerulus, 3 glomeruli/kidney, 3 kidneys/group). Effacement was described as an over 2.5 fold increase in mean width. Total and effaced foot processes were counted in NTS treated or control treated Angptl4−/− mice.

Studies with Archived Human Samples

Immunostaining of archived human kidney biopsies (n=5 biopsies per condition) was conducted on samples obtained via IRB approved protocols at the Instituto Nacional de Cardiologia, Mexico City. Control kidney biopsies used for these studies were sex and age matched protocol pre-transplant biopsies. Archival human sera for 2D gel electrophoresis and Western blot (n=4 samples/condition) were obtained from a previously published study (29).

Generation of Transgenic Rats aP2-Angptl4 TG rats (adipose tissue specific) construct was generated in the vector that contained the 5.4 Kb mouse aP2 promoter construct (30) (purchased from Addgene Inc. Cambridge Mass. USA) by cloning the rat Angptl4 cDNA (including the signal sequence) with a C-terminal V5 tag at the NotI site just upstream of the polyA tail.

Transgenic rats were generated by microinjection of the digested DNA constructs into fertilized Sprague Dawley eggs (conducted at University of Michigan), implantation into pseudopregnant host Sprague Dawley females, and the resulting offsprings were genotyped by routine PCR and TaqMan genomic DNA real time PCR strategy using construct specific and control genomic prolactin primer and probe combinations (FIG. 3). Three founder lines for adipose tissue specific expression were generated. Data from aP2-Angptl4 TG rat line 375 (3 copies), both stable over 4 generations, are presented. Urinary total protein was assessed using the Bradford method (Biorad laboratories, Hercules Calif. USA), and albuminuria by ELISA (Bethyl laboratories, Montgomery Tex. USA).

In Vitro Studies with GEnCs

For GEnC studies, cultured rat GEnCs (32) were grown to 75% confluence in 6 well plates (n=3 wells/condition), washed twice with warm PBS, serum free RPMI containing 200 μM $H_2O_2$, along with 600 μg/well of control stable cell line supernatant, or Angptl4-HEK293 stable cell line supernatant, or supernatant from ManNAc treated Angptl4-HEK293 cell line. Wells were sampled at 24, 36 and 48 hours. LDH release was measured using the cytotoxicity detection kit (Roche Diagnostics, Mannheim Germany). OD 492 values were expressed as a ratio of readings from wells in which no $H_2O_2$ or stable cell line supernatant was added.

Statistical Analysis

Analysis of difference in proteinuria or gene expression involving three or more groups was conducted by ANOVA with post analysis testing using GraphPad InStat software, Version 3.05. For comparison of two groups, the unpaired Students t test in Microsoft Excel 2003 was used.

REFERENCES

1. Falk R, Jennette C, Nachman P H. Primary glomerular disease. In The Kidney, Brenner B M, editor, 6$^{th}$ edition, 1263-1349 (2000).
2. Gutman, A. & Shafrir, E. Adipose tissue in experimental nephrotic syndrome. *Am. J. Physiol.* 205, 702-706 (1963).
3. Vaziri, N. D. Molecular mechanisms of lipid disorders in nephrotic syndrome. *Kidney Int.* 63, 1964-1976 (2003).
4. Shearer, G. C. & Kaysen G A. Endothelial bound lipoprotein lipase (LpL) depletion in hypoalbuminemia results from decreased endothelial binding, not decreased secretion. *Kidney Int.* 70, 647-653 (2006).
5. Reaven, E. P., Kolterman, O. G. & Reaven, G. M. Ultrastructural and physiological evidence for corticosteroid-induced alterations in hepatic production of very low density lipoprotein particles. *J. Lipid Res.* 15, 74-83 (1974).
6. Tsukamoto, Y., Kokubo, T., Horii, A., Moriya, R. & Kobayashi, Y. Lipoprotein derangement during steroid treatment in minimal-change nephrotic syndrome. *Nephron* 73, 606-612 (1996).
7. Liu, G., Clement, L., Kanwar, Y. S., Avila-Casado, C. & Chugh, S. S. ZHX proteins regulate podocyte gene expression during the development of nephrotic syndrome. *J. Biol. Chem.* 281, 39681-39692 (2006).
8. Yoon, J. C. et al. Peroxisome proliferator-activated receptor gamma target gene encoding a novel angiopoietin-related protein associated with adipose differentiation. *Mol. Cell. Biol.* 20, 5343-5349 (2000).
9. Kersten, S. et al. Characterization of the fasting-induced adipose factor FIAF, a novel peroxisome proliferator-activated receptor target gene. *J. Biol. Chem.* 275, 28488-28493 (2000).
10. Kim, I. et al. Hepatic expression, synthesis and secretion of a novel fibrinogen/angiopoietin-related protein that prevents endothelial-cell apoptosis. *Biochem. J.* 346, 603-610 (2000).
11. Yoshida, K., Shimizugawa, T., Ono, M. & Furukawa, H. Angiopoietin-like protein 4 is a potent hyperlipidemia-inducing factor in mice and inhibitor of lipoprotein lipase. *J. Lipid Res.* 43, 1770-1772 (2002).
12. Ge, H., et al. Oligomerization and regulated proteolytic processing of angiopoietin-like protein 4. *J. Biol. Chem.* 279, 2038-2045 (2004).
13. Ge, H., Yang, G., Yu, X., Pourbahrami, T. & Li, C. Oligomerization state-dependent hyperlipidemic effect of angiopoietin-like protein 4. *J. Lipid Res.* 45, 2071-2079 (2004).
14. Romeo, S., et al. Population-based resequencing of ANGPTL4 uncovers variations that reduce triglycerides and increase HDL. *Nat. Genet.* 39, 513-516 (2007).
15. Romeo, S. et al. Rare loss-of-function mutations in ANGPTL family members contribute to plasma triglyceride levels in humans. *J. Clin. Invest.* 119:70-79 (2009).
16. Eremina, V., et al. VEGF inhibition and renal thrombotic microangiopathy. *N. Engl. J. Med.* 358, 1129-1136 (2008).
17. Davis, B., et al. Podocyte-specific expression of angiopoietin-2 causes proteinuria and apoptosis of glomerular endothelia. *J. Am. Soc. Nephrol.* 18, 2320-2329 (2007).
18. Avila-Casado, C., et al. Proteinuria in rats induced by serum from patients with collapsing glomerulopathy. *Kidney Int.* 66, 133-143 (2004).
19. Mandard, S., et al. The fasting-induced adipose factor/angiopoietin-like protein 4 is physically associated with lipoproteins and governs plasma lipid levels and adiposity. *J. Biol. Chem.* 281:934-944 (2006).
20. Clement, L., et al. Early changes in gene expression that influence the course of primary glomerular disease. *Kidney Int.* 72, 337-347 (2007).
21. Cazes, A. et al. Extracellular matrix-bound angiopoietin-like 4 inhibits endothelial cell adhesion, migration, and sprouting and alters actin cytoskeleton. *Circ. Res.* 99, 1207-1215 (2006).
22. Malicdan, M. C., Noguchi, S., Hayashi, Y. K., Nonaka, I. & Nishino, I. Prophylactic treatment with sialic acid metabolites precludes the development of the myopathic phenotype in the DMRV-hIBM mouse model. *Nat. Med.* 15, 690-695 (2009).
23. Galeano, B. et al. Mutation in the key enzyme of sialic acid biosynthesis causes severe glomerular proteinuria and is rescued by N-acetylmannosamine. J. Clin. Invest. 117, 1585-1594 (2007).
24. Ruge, T. et al. Lipoprotein lipase in the kidney: activity varies widely among animal species. *Am. J. Physiol. Renal Physiol.* 287, F1131-F1139 (2004).
25. Koliwad, S. K. et al. Angiopoietin-like 4 (ANGPTL4/FIAF) is a direct glucocorticoid receptor target and participates in glucocorticoid-regulated triglyceride metabolism. *J. Biol. Chem.* 284, 25593-25601 (2009).
26. Liu, G. at al. Nephi and nephrin interaction in the slit diaphragm is an important determinant of glomerular permeability. *J. Clin. Invest.* 112, 209-221 (2003).
27. Dijkman, H. B. P. M., Mentzel, S., de Jong, A. S. & Assmann, K. J. M. RNA in situ hybridization using digoxigenin-labeled cRNA probes. *Biochemica* 2, 23-27 (1995).
28. Isogai, S., Mogami, K., Shiina, N. & Yoshino, G. Initial ultrastructural changes in pore size and anionic sites of the glomerular basement membrane in streptozotocin-induced diabetic rats and their prevention by insulin treatment. *Nephron.* 83, 53-58 (1999).
29. Bakker, W. W. et al. Altered activity of plasma hemopexin in patients with minimal change disease in relapse. *Pediatr. Nephrol.* 20, 1410-1415 (2005).
30. Graves, R. A., Tontonoz, P., Platt, K. A., Ross, S. R. & Spiegelman, B. M. Identification of a fat cell enhancer: analysis of requirements for adipose tissue-specific gene expression. *J. Cell Biochem.* 49, 219-224 (1992).
31. Yoshida, K., Ono, M., Koishi, R. & Furukawa, H. Characterization of the 5' regulatory region of the mouse angiopoietin-like protein 4. *Vet. Res. Commun.* 28, 299-305 (2004).
32. Zeng, L. et al. HMG CoA reductase inhibition modulates VEGF-induced endothelial cell hyperpenneability by preventing RhoA activation and myosin regulatory light chain phosphorylation. *FASEB J.* 19, 1845-1847 (2005).
33. Romeo, S. et al. Population-based resequencing of ANGPTL4 uncovers variations that reduce triglyceride and increase HDL. Nature Genetics, 39, 513-517 (2007).
34. Yin, Wu et al. Genetic variation in Angptl4 provides insight into protein processing and function, J. Biol. Chem., 284, 13213-13222 (2009).

What is claimed:

1. A method for the treatment or reduction prior to onset of proteinuria in a subject, said method comprising the step of administering to the subject a therapeutically effective amount of an Angptl4 polypeptide selected from the group consisting of: positions 1-187 of SEQ ID NO: 1, positions 1-182 of SEQ ID NO: 3, and an Angptl4 derivative thereof; wherein the Angptl4 derivative thereof comprises one or more substitutions at positions 39, 40, 76, 80, and 161-164.

2. The method of claim 1 wherein the Angptl4 polypeptide comprises the sequence of SEQ ID NOS: 1 or 3.

3. The method of claim 1, wherein the Angptl4 derivative has decreased lipoprotein lipase inhibitory activity, is resistant to cleavage, or a combination of the foregoing.

4. The method of claim 1, wherein the Angptl4 derivative has decreased lipoprotein lipase inhibitory activity.

5. The method of claim 4, wherein the Angptl4 derivative contains an amino acid substitution at position 40 with respect to the wild-type Angptl4 polypeptide.

6. The method of claim 5, wherein the Angptl4 derivative contains K at position 40, A at position 40, K at position 39, A at position 39, or a combination of the foregoing.

7. The method of claim 1, wherein the Angptl4 derivative is resistant to cleavage.

8. The method of claim 7, wherein the Angptl4 derivative contains an amino acid substitution at one or more of positions 161, 162, 163 or 164 with respect to the wild-type Angptl4 polypeptide.

9. The method of claim 7, wherein one or more of positions 161, 162 and 164 of the Angptl4 derivative is a neutral amino acid, and position 163 of the Angptl4 derivative is a neutral amino acid.

10. The method of claim 7, wherein the residue at one or more of positions 161, 162 and 164 of the Angptl4 derivative is D, R, K, G, A, V or S; and the residue at position 163 of the Angptl4 derivative is D, R, K, G, A, V or S.

11. The method of claim 1, wherein the Angptl4 derivative has the sequence of SEQ ID NOS: 9 or 10, wherein $X_{39}$ is D, $X_{40}$ is A or K, $X_{76}$ and $X_{80}$ are C, and $X_{161}$, $X_{162}$, $X_{163}$ and $X_{164}$ are independently selected from D, R, K, G, A; V or S.

12. The method of claim 1, wherein the Angptl4 derivative has the sequence of SEQ ID NOS: 9 or 10; wherein $X_{39}$ is D; $X_{40}$ is A or K; one of $X_{76}$ and $X_{80}$ is A or S and the other of $X_{76}$ and $X_{80}$ is C and $X_{161}$; $X_{162}$, $X_{163}$ and $X_{164}$ are independently selected from D, R, K, G, A, V or S.

13. The method of claim 1, wherein the Angptl4 derivative has the sequence of SEQ ID NOS: 9 or 10; wherein $X_{39}$ is A or K; $X_{40}$ is E; $X_{76}$ and $X_{80}$ are C; and $X_{161}$, $X_{162}$, $X_{163}$ and $X_{164}$ are independently selected from D, R, K, G, A, V or S.

14. The method of claim 1, wherein the Angptl4 derivative has the sequence of SEQ ID NOS: 9 or 10; wherein $X_{39}$ is A or K; $X_{40}$ is E; one of $X_{76}$ and $X_{80}$ is A or S and the other of $X_{76}$ and $X_{80}$ is C; and $X_{161}$, $X_{162}$, $X_{163}$ and $X_{164}$ are independently selected from D, R, K, G, A, V or S.

15. The method of claim 1, wherein the Angptl4 derivative has the sequence of SEQ ID NOS: 9 or 10; wherein $X_{39}$ is D; $X_{40}$ is K; $X_{80}$ is C, or one of $X_{76}$ and $X_{80}$ is A or S and the other of $X_{76}$ and $X_{80}$ is C; and $X_{161}$, $X_{162}$, $X_{163}$ and $X_{164}$ are independently selected from D, R, K, G, A, V or S, provided that at least one of $X_{161}$, $X_{162}$, $X_{163}$ and $X_{164}$ is an amino acid not found in the corresponding positions of SEQ ID NOS: 1 or 3.

16. The method of claim 1, wherein the Angptl4 derivative has the sequence of SEQ ID NOS: 9 or 10; wherein $X_{39}$ is K; $X_{40}$ is D; $X_{80}$ is C, or one of $X_{76}$ and $X_{80}$ is A or S and the other of $X_{76}$ and $X_{80}$ is C; and $X_{161}$, $X_{162}$, $X_{163}$ and $X164$ are independently selected from D, R, K, G, A, V or S.

17. The method of claim 1, wherein the Angptl4 polypeptide is sialylated.

18. The method of claim 1, in which the Angptl4 polypeptide is administered for at least two consecutive days.

19. The method of claim 1, wherein said proteinuria is due to kidney disease.

20. The method of claim 1, wherein said proteinuria is due to diabetic nephropathy or focal segmental glomerulosclerosis.

* * * * *

UNITED STATES PATENT AND TRADEMARK OFFICE
CERTIFICATE OF CORRECTION

PATENT NO.        : 9,475,850 B2
APPLICATION NO.   : 13/364962
DATED             : October 25, 2016
INVENTOR(S)       : Sumant S. Chugh Page 1 of 1

It is certified that error appears in the above-identified patent and that said Letters Patent is hereby corrected as shown below:

Replace the following paragraph found in Column 1, Lines 19-22:

This invention was made with government support under grant numbers NIH 7R01DK077073-02 and NIH 1R56DK077073-01 awarded by the National Institutes of Health. The government has certain rights in the invention.

With this paragraph:

"This invention was made with government support under grant number DK077073 awarded by the National Institutes of Health. The government has certain rights in the invention."

Signed and Sealed this
Eighth Day of May, 2018

Andrei Iancu
*Director of the United States Patent and Trademark Office*